United States Patent
Kasai et al.

(10) Patent No.: US 7,977,116 B2
(45) Date of Patent: Jul. 12, 2011

(54) ANALYSIS METHOD AND ANALYSIS APPARATUS

(75) Inventors: Shintaro Kasai, Tokyo (JP); Toshihiko Ouchi, Sagamihara (JP); Haruko Yoneyama, Saitama (JP); Masatsugu Yamashita, Wako (JP)

(73) Assignee: Canon Kabushiki Kaisha, Tokyo (JP)

( * ) Notice: Subject to any disclaimer, the term of this patent is extended or adjusted under 35 U.S.C. 154(b) by 759 days.

(21) Appl. No.: 11/716,702

(22) Filed: Mar. 12, 2007

(65) Prior Publication Data
US 2007/0229094 A1 Oct. 4, 2007

(30) Foreign Application Priority Data

Mar. 17, 2006 (JP) ................................. 2006-074927
Jun. 29, 2006 (JP) ................................. 2006-178886
Aug. 28, 2006 (JP) ................................. 2006-231393
Dec. 26, 2006 (JP) ................................. 2006-349234

(51) Int. Cl.
*G01N 27/00* (2006.01)
*G01N 21/00* (2006.01)

(52) U.S. Cl. ............ 436/164; 436/527; 436/535; 435/4; 356/301; 356/326; 422/82.09; 422/91

(58) Field of Classification Search ................ 436/6, 64, 436/161, 162
See application file for complete search history.

(56) References Cited

U.S. PATENT DOCUMENTS

| | | | |
|---|---|---|---|
| 4,305,723 A * | 12/1981 | Kolber et al. | ................... 436/47 |
| 4,778,846 A * | 10/1988 | Sitrin et al. | ................... 525/54.1 |
| 5,032,975 A | 7/1991 | Yamamoto et al. | |
| 5,586,131 A | 12/1996 | Ono et al. | |
| 5,659,560 A | 8/1997 | Ouchi et al. | |
| 5,699,373 A | 12/1997 | Uchida et al. | |
| 5,764,670 A | 6/1998 | Ouchi | |
| 6,313,251 B1 * | 11/2001 | Toh et al. | ...................... 526/308 |

(Continued)

FOREIGN PATENT DOCUMENTS

JP 5-209836 8/1993

(Continued)

OTHER PUBLICATIONS

Taday, P.F., Applications of terahertz spectroscopy to pharmaceutical sciences, 2003, Phil. Trans. R. Soc. Lond. A, 362, p. 351-364.*

(Continued)

*Primary Examiner* — Krishnan S Menon
*Assistant Examiner* — Allison Gionta
(74) *Attorney, Agent, or Firm* — Fitzpatrick, Cella, Harper & Scinto

(57) ABSTRACT

Provided are an analysis method and an analysis apparatus that can perform analysis of a substance and information obtainment with relatively high accuracy and reproducibility without previously allowing a carrier to carry a reagent for a color reaction. In the analysis method and the analysis apparatus, the information on an analyte is obtained by using an electromagnetic wave of a frequency including a frequency band which is at least a part of a frequency range of 30 GHz or more and 30 THz or less. A non-fibrous, isotropic porous material is allowed to hold the analyte, the analyte held by the porous material is irradiated with the electromagnetic wave, a change in the propagation state of the electromagnetic wave due to transmission through or reflection by the porous material is detected and information on the analyte is obtained based on the result of the detection.

11 Claims, 17 Drawing Sheets

U.S. PATENT DOCUMENTS

| | | |
|---|---|---|
| 6,661,519 B2 | 12/2003 | Fukasawa .................... 356/432 |
| 6,854,901 B1 | 2/2005 | Ouchi |
| 7,062,116 B2 | 6/2006 | Ouchi |
| 7,244,934 B2 | 7/2007 | Arnone et al. ............. 250/336.1 |
| 7,248,995 B2 | 7/2007 | Itsuji et al. |
| 2006/0039431 A1 | 2/2006 | Sekiguchi et al. |
| 2006/0085160 A1 | 4/2006 | Ouchi |
| 2006/0188398 A1 | 8/2006 | Yano et al. |
| 2006/0197021 A1 | 9/2006 | Ouchi |
| 2006/0214176 A1 | 9/2006 | Ouchi et al. |
| 2006/0227340 A1 | 10/2006 | Shioda et al. |
| 2006/0244629 A1 | 11/2006 | Miyazaki et al. |
| 2007/0030115 A1 | 2/2007 | Itsuji et al. |
| 2007/0195921 A1 | 8/2007 | Ouchi |
| 2007/0215808 A1 | 9/2007 | Sekiguchi et al. |
| 2007/0235718 A1 | 10/2007 | Kasai et al. |
| 2008/0014580 A1* | 1/2008 | Alfano et al. .................... 435/6 |

FOREIGN PATENT DOCUMENTS

| | | |
|---|---|---|
| JP | 2002-005828 | 1/2002 |
| JP | 2005-517925 | 6/2005 |

OTHER PUBLICATIONS

Yu et al., THz absorption spectrum of Bacillus subtilis spores, 2005, The Society of Photo-Optical Instrumentation Engineers, vol. 5727, pp. 19-23.*

Sakai, K., 3.5 Attenuated Total Reflection Spectroscopy, 2005, Terahertz Optoelectronics, pp. 242-247.*

Globus et al., Terahertz Fourier Transform characterization of biological materials in a liquid phase, Jul. 21, 2006, J. Phys. D: Appl. Phys., 39, 3405-3413.*

U.S. Appl. No. 11/632,958, filed Jan. 19, 2007.
U.S. Appl. No. 10/587,261, filed Jul. 26, 2006.
U.S. Appl. No. 10/833,781, filed Mar. 27, 2007.
U.S. Appl. No. 11/727,588, filed Mar. 27, 2007.

* cited by examiner

FIG. 1
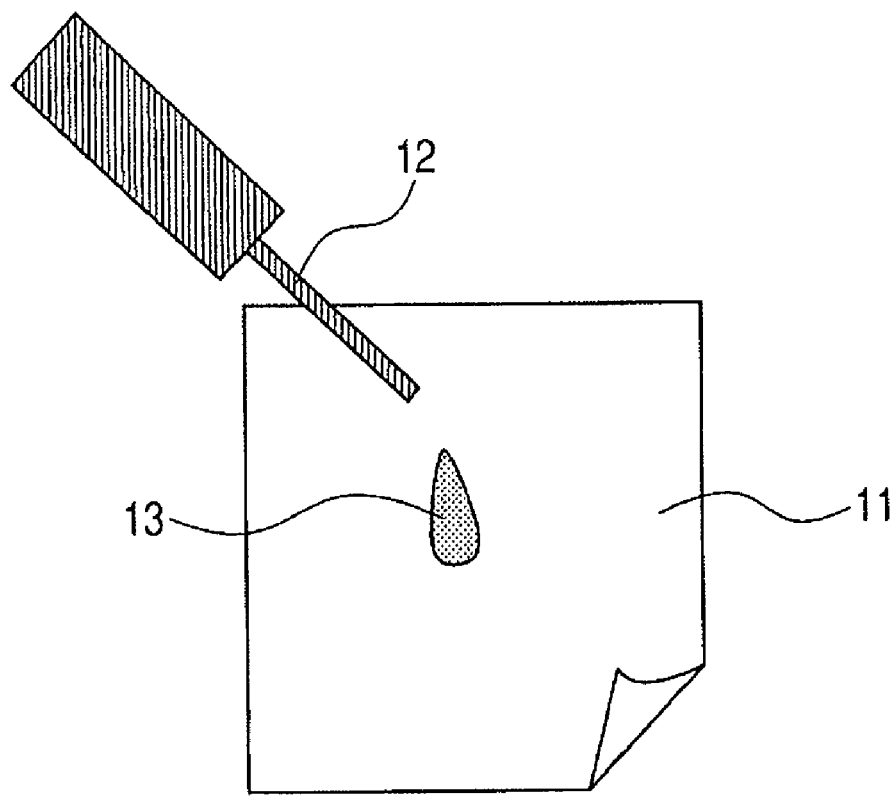
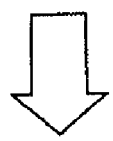
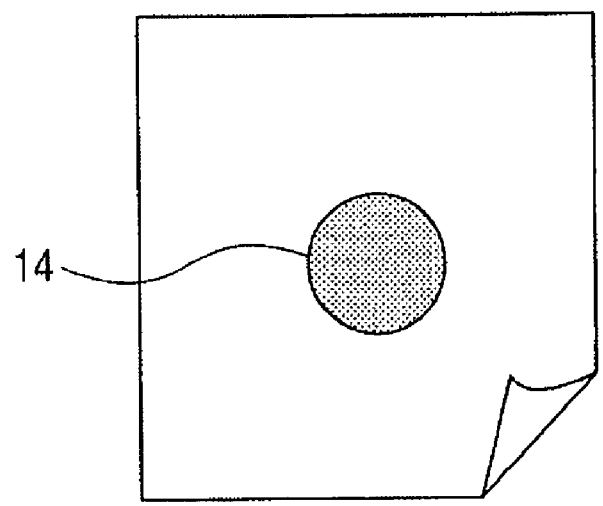

| FIG. 17A |
|----------|
| FIG. 17B |

FIG. 17A

TABLE 1

| MAIN COMPONENT OF MEMBRANE FILTER | AMPLITUDE TRANSMITTANCE | | | PORE DIAMETER | FILM THICKNESS | USE | FEATURE | FILTRATION RATE | UNIFORMITY (ECCENTRICITY) | INDEX INDICATIVE OF TRANSMITTANCE CONSTANCY | MODE OF POROSITY |
|---|---|---|---|---|---|---|---|---|---|---|---|
| | 0.5THz | 1.0THz | 2.0THz | | | | | | *1 | *2 | |
| POLYPROPYLENE | 100 | 98 | 96 | 0.45μm | 114μm | BOTH AQUEOUS SOLUTIONS AND SOLVENTS ARE USABLE | LOW ADSORPTION OF PROTEIN | LARGE | 1.02 | 24.3 | SPONGE-SHAPED |
| POLYSULFONE | 97 | 97 | 100 | 0.45μm | 145μm | BACTERIA-REDUCING FILTRATION FOR ORGANISM AND DRUG | LOW ADSORPTION OF PROTEIN | LARGE | 1.09 | 32.0 | SPONGE-SHAPED |
| POLYETHERSULFONE | 98 | 96 | 100 | 0.45μm | 140μm | BACTERIA-REDUCING FILTRATION FOR ORGANISM AND DRUG | LOW ADSORPTION OF BIOMOLECULES | LARGE | 1.00 | 47.5 | PARTICU-LATE |
| NYLON | 97 | 96 | 95 | 0.45μm | 127μm | SUITABLE FOR ORGANIC SOLVENTS | HYDROPHILICITY OF MEMBRANE ITSELF | LARGE | 1.01 | 47.5 | SPONGE-SHAPED |
| POLYVINYLIDENE DIFLUORIDE | 98 | 96 | 84 | 0.45μm | 147μm | APPLIED TO NUCLEIC ACID AND PROTEIN | RESISTANCE AGAINST BIOLOGICAL SOLVENTS | NO FILTRATION | UNEVALUABLE | 6.79 | FIBROUS/PARTICU-LATE |

TO FIG. 17B

FIG. 17B  FROM FIG. 17A

| Material | | | | | | Application | Property | | *1 | *2 | Shape |
|---|---|---|---|---|---|---|---|---|---|---|---|
| NITROCELLULOSE | 97 | 91 | 85 | 0.2 μm | 145 μm | WESTERN TRANSFER | HIGH BONDABILITY TO PROTEIN AND NUCLEIC ACID | VERY SMALL | 1.16 | 7.50 | FIBROUS |
| CELLULOSE | 95 | 89 | 70 | 20-25 μm | 0.21 mm | ANALYSIS OF ALUMINUM ETC | FOR GELATINOUS SEDIMENTS | VERY LARGE | 1.11 | 3.52 | FIBROUS |
| GLASS FIBER | 98 | 90 | 80 | 1.6 μm | 0.26 mm | MONITORING OF AIR POLLUTION | RAPID FILTRATION, HOLDING OF FINE PARTICLES | VERY LARGE | UNCLEAR | 4.94 | FIBROUS |
| CELLULOSE MIXED ESTER | 98 | 95 | 88 | 0.8 μm | 152 μm | INSPECTION OF MICROORGANISMS | HIGH CAPTURE RATE | SMALL | 1.36 | 9.40 | FIBROUS SPONGE-SHAPED |
| QUARTZ FIBER | 98 | 99 | 82 |  | 0.45 mm | ATOMIC ABSORPTION SPECTROMETRY AND ATOMIC EMISSION SPECTROMETRY | LOW BACKGROUND | VERY LARGE | 1.12 | 6.13 | FIBROUS |
| MODIFIED POLYETHERSULFONE | 97 | 95 | 100 | 0.8 μm | 140 μm | CAPABLE OF ELUTION OF BIOMOLECULES | ADSORPTION OF DNA | LARGE | 1.03 | 31.3 | PARTICULATE |

THE COLUMN MARKED WITH *1 SHOWS AN INDEX INDICATING THE UNIFORMITY OF SOARKING. ECCENTRICITY AS A RATIO OF MAJOR AXIS AND MINOR AXIS OF AN ELLIPSE IS USED. INDEX OF 1.0 INDICATES A PERFECT CIRCLE. BECAUSE POLYVINYLIDENE DIFLUORIDE DOES NOT SOAK, THE UNIFORMITY CAN NOT BE EVALUATED. BECAUSE THE BOUNDARY OF A REGION WHERE GLASS FIBER SOAKS IS UNCLEAR, THE UNIFORMITY CAN NOT BE UNEVALUATED.

THE COLUMN MARKED WITH *2 SHOWS AN INDEX INDICATING THE CONSTANCY OF TRANSMITTANCE. THIS INDEX IS THE TRANSMITTANCE ABBE NUMBER DEFINED IN THE SPECIFICATION.

ANALYSIS METHOD AND ANALYSIS APPARATUS

BACKGROUND OF THE INVENTION

1. Field of the Invention

The present invention relates to a technique directed to an analysis method that involves using a porous material and an electromagnetic wave and performing analysis (detection, identification and the like) of an analyte held by the porous material by irradiating the analyte with the electromagnetic wave. More particularly, the present invention relates to an analysis method and an analysis apparatus for performing analysis of or information obtainment on an objective material by using an electromagnetic wave of a frequency including a frequency band which is at least a part of a frequency range of 30 GHz to 30 THz (hereinafter, referred to as "terahertz wave").

2. Description of the Related Art

There have hitherto been used methods that involve dropping droplet(s) of an analyte on a carrier such as of a porous material (filter paper, membrane filter, sponge-shaped object), and optically detecting a color reaction between a reagent previously carried by the carrier and the analyte to examine the analyte.

For example, Japanese Patent Application Laid-Open No. H05-209836 discloses a technique that involves dropping a droplet of an analyte on a carrier made of a fibrous porous material or a non-fibrous porous material having a reagent previously carried thereon, and quantitatively detecting a color reaction by use of a white-light source, a color filter and a photodetector. In this technique, the carrier made of the fibrous porous material or non-fibrous porous material having the analyte dropped thereon is irradiated with white light, and the wavelength of light scattered by the porous material is selected by the color filter. Then, by measuring the intensity of the light transmitted through the color filter with the photodetector, the extent of the color reaction is estimated.

Meanwhile, recent years have seen active development of techniques that utilize terahertz wave. In particular, the terahertz wave has photon energy of the same level as the energy of the skeletal vibration in a molecule or the energy of the interaction of molecules. Therefore, the terahertz wave is used in techniques of performing analysis of a substance from a spectrum obtained by spectroscopic means.

With respect to such techniques, Japanese Patent Application Laid-Open No. 2002-5828 discloses a method of determining the complex refractive index of a substance by using the terahertz wave. In the method, a comparison is made between the amplitude/phase obtained by Fourier transform of a time waveform of a terahertz wave transmitted through or reflected from the substance and the amplitude/phase obtained by Fourier transform of a time waveform of a terahertz wave (reference wave) when the substance is absent. Further, the result of the comparison is substituted into an equation to determine the complex refractive index of the substance.

There is known a technique using the above-mentioned method that involves mixing microcrystalline powder of a sugar such as glucose with polyethylene powder, forming the powder mixture into a pellet by application of pressure, and irradiating the pellet with a terahertz wave, thereby obtaining a transmission spectrum in the terahertz region of the sugar such as glucose. Furthermore, there is also known a technique such that after an aqueous solution of DNA has been dropped dropwise on a sapphire substrate, the DNA precipitated on the sapphire substrate is irradiated with a terahertz wave to determine the transmittance of the DNA, whereby a determination is made as to whether the DNA is single stranded or double stranded based on a difference in the transmittance.

Also, Japanese Patent Application Laid-Open No. 2005-517925 discloses a method that involves dropping a droplet of an aqueous solution of glucose on cellulose nitrate (nitrocellulose) filter paper and drying the paper, and then irradiating the dried paper with a terahertz wave and obtaining a spectrum of the glucose from the terahertz wave transmitted though the paper.

As described above, the technique disclosed in Japanese Patent Application Laid-Open No. H05-209836 requires that a reagent be previously carried by a carrier. Further, in some cases a reagent is expensive and some kinds of reagents are difficult to handle because of their toxicity. Also, the technique disclosed in Japanese Patent Application Laid-Open No. H05-209836 essentially requires a color reaction in order to examine an analyte, and only an analyte that causes a color reaction with a previously carried reagent, which is inconvenient.

Moreover, in the technique disclosed in Japanese Patent Application Laid-Open No. 2005-517925, a solution that serves as an analyte does no soak uniformly and nonuniform distribution is liable to be caused. This is considered because the cellulose nitrate filter paper used is formed of a fibrous substance, with the result that the liquid substance is nonuniformly absorbed thereby when dropped. Such nonuniform distribution of the analyte gives spatial nonuniformity to the transmitted terahertz wave and may sometimes exert an adverse effect, such as noise, on the frequency region when the time waveform of the transmitted terahertz wave is Fourier transformed, which is undesirable for accurate measurement. In addition, the amplitude transmittance of cellulose nitrate filter paper for a terahertz wave of a frequency of 2.0 THz or more is low and the amplitude transmittance has a frequency dependence, which may have an adverse effect on the accuracy of measurement.

SUMMARY OF THE INVENTION

In order to solve the above-mentioned problems, the present invention provides an analysis method of obtaining information on an analyte by using an electromagnetic wave of a frequency including a frequency band which is at least a part of a frequency range of 30 GHz or more and 30 THz or less, which includes allowing a non-fibrous, isotropic porous material to hold an analyte; irradiating the analyte held by the porous material with the electromagnetic wave; and detecting a change in propagation state of the electromagnetic wave due to transmission through or reflection by the porous material, and obtaining information about the analyte based on a result of the detection. The definition of the non-fibrous, isotropic porous material will be described later.

Also, in view of the above mentioned problems to be solved, the present invention provides an analyte holding member for holding the analyte from which information is obtained by the analysis method set forth above, which includes a partition wall for holding the analyte in a region and the porous material disposed inside the partition wall and has, in a region other than the region defined by the partition wall, at least a member which does not transmit the electromagnetic wave.

Also, in view of the above-mentioned problems to be solved, the present invention provides an analysis apparatus for performing the analysis method set forth above, which includes an electromagnetic wave irradiating unit for irradiating the porous material with the electromagnetic wave, and an electromagnetic wave detecting unit for detecting the change in the propagation state of the electromagnetic wave due to the transmission through or the reflection by the porous material. For example, in the case of the configuration shown in FIG. 2, the electromagnetic wave radiating unit is constituted by the elements 21, 3, 25 and the like, and the electromagnetic wave detecting unit is constituted by the elements 21, 22, 24 and the like.

Hereinafter, a description will be given of the principle of operation of the present invention and of the non-fibrous, isotropic porous materials used in the present invention. In the present invention, as the non-fibrous, isotropic porous material, there is used, for example, a porous material formed of a particulate structure. This porous material formed of a particulate structure is such that a large number of fine particles are dispersed with isotropy (a property that the filling ratio of the fine particles is almost constant in any region), the fine particles are in contact with each other at points or surfaces, and a fibrous structure as described later is not substantially contained. Further, there is also used, for example, a porous material formed of a sponge-shaped structure. This porous material formed of a sponge-shaped structure is such that a large number of voids are dispersed with isotropy (a property that the volume ratio of the voids is almost constant in any region) in a matrix and a fibrous structure as described later is not substantially contained. For instance, the porous material formed of a particulate structure is a porous material 111 with a structure containing a particulate structure 110 as shown in FIG. 10 and the porous material formed of a sponge-shaped structure is a porous material 121 with a structure containing a large number of voids 120 dispersed with isotropy as shown in FIG. 11. Such porous materials bring about a uniformly distributed state of a liquid analyte as will be described below, which is desirable.

On the other hand, a fibrous porous material containing a fibrous structure (for example, those shown in FIGS. 12 and 13) has an undesirable tendency. In FIGS. 12 and 13, a porous material 131 contains a fibrous structure 130 and a porous material 141 contains a fibrous structure 140 and a particulate structure 142. The reason is described with reference to FIGS. 14 and 15. As shown in FIG. 14, when a liquid analyte is dropped as a droplet on a porous material 151, in a case where the porous material 151 is a non-fibrous, isotropic porous material, the liquid analyte becomes uniformly distributed as indicated by reference numeral 152 and takes a shape similar to a perfect circle.

However, as shown in FIG. 15, in the case of a porous material 161 containing a fibrous structure, the liquid analyte becomes nonuniformly distributed as indicated by reference numeral 162 and becomes elliptical. Here, a liquid analyte was dropped as a droplet on a porous material containing a fibrous structure, such as nitrocellulose, cellulose, glass fiber, and quartz fiber, and an investigation was carried out as shown in Table 1 of FIGS. 17A and 17B. As a result, it was found that the extent of the nonuniformity is 1.11 or more in terms of the value (eccentricity) obtained by (major axis length)÷(minor axis length) of the elliptic distribution. On the other hand, as similarly shown in Table 1, in the case of a non-fibrous, isotropic porous material such as polypropylene, polysulfone, polyethersulfone, or nylon, the above-mentioned eccentricity is less than 1.11. Therefore, this can bring about a more uniform distribution and is desirable.

When a liquid analyte is nonuniformly distributed, as described in connection with the above-described problems, spatial nonuniformity occurs in the electromagnetic field distribution of a transmitted terahertz wave and an unnecessary noise signal is generated when the time waveform of the transmitted terahertz wave is Fourier transformed. Therefore, this is undesirable.

In an experiment carried out by the present inventors, as shown in Table 1 of FIGS. 17A and 17B, the amplitude transmittance tended to become less than 90% with an electromagnetic wave of 2.0 THz in the case of a porous material containing a fibrous structure such as of cellulose acetate. It also became apparent that the value indicating the constancy of the amplitude transmittance herein defined and given by Equation 1 below is less than 10. This is not preferable for analysis requiring high accuracy and reproducibility.

$$v' = \frac{|T_M - 1|}{|T_L - T_H|} \quad \text{[Equation 1]}$$

The value v' of Equation 1 is the absolute value of a value obtained by subtracting 1 from the amplitude transmittance $T_M$ of a frequency near the middle of a terahertz wave frequency band used in the measurement and dividing the resulting value by a difference between the amplitude transmittance $T_H$ at the upper limit of the frequency band and the amplitude transmittance $T_L$ at the lower limit of the frequency band. This value becomes an index indicating the degree of constancy of amplitude transmittance with respect to frequency. The higher this value, the smaller the frequency dependence of the amplitude transmittance. For example, when this value is infinity as one limit value, the amplitude transmittance does not depend on frequency. The index of the degree of constancy of amplitude transmittance with respect to frequency, which is represented by Equation 1, was defined by referring to the Abbe number that indicates the frequency dependence of the refractive index used in the field of optical materials, and for the sake of convenience this index is hereinafter referred to as "transmittance Abbe number v'".

In contrast to the above-described porous material containing a fibrous structure, in a porous material that is formed of a non-fibrous isotropic structure and contains any of polypropylene, polysulfone, nylon and polyethersulfone, for example, the situation is as follows. That is, it was seen that the amplitude transmittance is 90% or more at 2.0 THz and that the value indicating the degree of constancy of amplitude transmittance given by Equation 1 is 20 or more (see Table 1 of FIGS. 17A and 17B) As is seen from Table 1, the value indicating the degree of constancy of amplitude transmittance is about 24 at minimum for porous materials included in the scope of the present invention and about 10 at most for those not included in the scope of the present invention. Therefore, if the transmittance Abbe number v', which is a value indicating the degree of constancy of amplitude transmittance, is 20 or more, such porous material can be said to be sufficiently desirable.

In summary, it has been seen that compared to a porous material containing a fibrous structure such as cellulose, a non-fibrous, isotropic porous material that contains at least one of polypropylene, polysulfone, nylon and polyethersulfone, which are exemplified as being desirable, is such that as described below. That is, it has been seen that the non-fibrous, isotropic porous material permits measurements in a wide region (a band with high amplitude transmittance is relatively wide) for a terahertz wave and that the signal noise ratio is high.

It is considered that the use of a material having a high amplitude transmittance for a terahertz wave is desirable so long as the material is a non-fibrous, isotropic porous material even when the material is other than polypropylene, polysulfone, nylon, and polyethersulfone, which are enumerated above. That is, it is considered that the same effect can be expected also when employing those other materials having a relatively high amplitude transmittance and a high degree of constancy of amplitude transmittance with respect to frequency, for example, those containing at least one of Teflon (registered trademark), polyolefin, polyethylene, polystyrene, ethylene tetrafluoride resins, which have small losses for a terahertz band.

On the basis of these experiment facts, the following can be said for the analyte holding means from the standpoints of amplitude transmittance, transmittance Abbe number, and the uniformity of holding of an analyte. That is, compared to a porous material containing a fibrous structure, a non-fibrous, isotropic porous material that uses a material having a high amplitude transmittance in bulk is desirable when made available for use in spectroscopy using a terahertz wave. Further, typical examples of the material having a high amplitude transmittance in bulk include those materials containing any of polypropylene, polysulfone, nylon, and polyethersulfone.

Accordingly, in the analysis method and the analysis apparatus of the present invention, a liquid analyte is held by using a non-fibrous, isotropic porous material that uses the material as described above, and analysis of the liquid analyte are performed utilizing a change in the propagation state of a terahertz wave with which the analyte is irradiated.

In the analysis method and analysis apparatus of the present invention, it is possible to perform analysis of a substance and to obtain information on the substance without allowing a reagent for a color reaction to be previously carried by a carrier. Therefore, it is possible to provide an analysis method and an analysis apparatus that are simple and economical. Furthermore, in the analysis method and analysis apparatus of the present invention, a non-fibrous, isotropic porous material that uses the material as described above is used and, therefore, it is possible to provide an analysis method and an analysis apparatus that have higher accuracy and higher reproducibility.

Further features of the present invention will become apparent from the following description of exemplary embodiments with reference to the attached drawings.

BRIEF DESCRIPTION OF THE DRAWINGS

FIG. 1 is a diagram illustrating a method of preparing a spectroscopic sample using a membrane filter.

FIG. 17 which is composed of FIGS. 17A and 17B are Table 1 showing the transmittances of various kinds of membrane filters with respect to a terahertz wave.

BRIEF DESCRIPTION OF THE DRAWINGS

Figure 2:
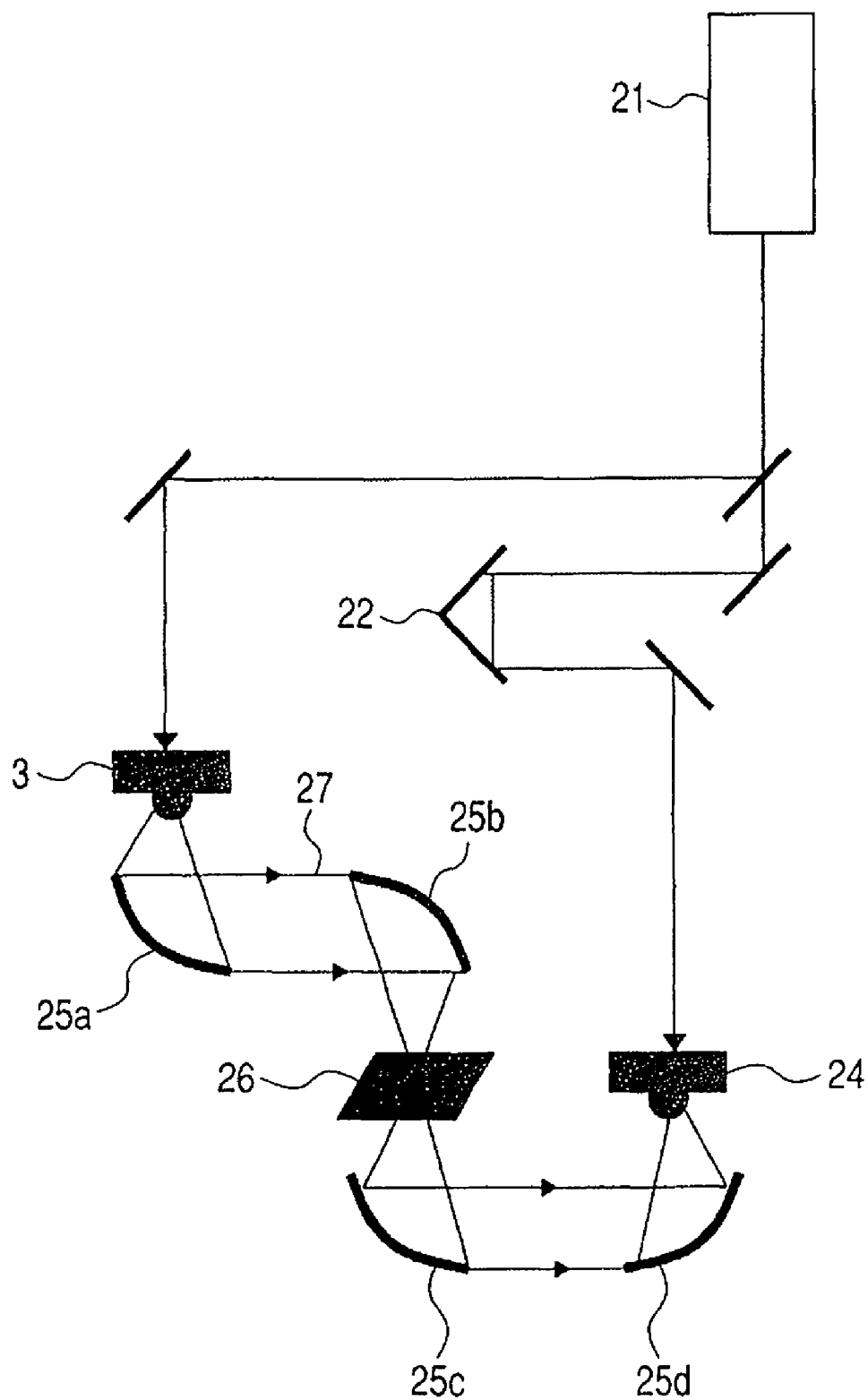
FIG. 2 is a diagram illustrating an optical arrangement for performing material analysis with a terahertz wave.

Modes for carrying out the analysis method and analysis apparatus of the present invention will be described below. In one embodiment of the present invention, first, an analyte is allowed to be held by a non-fibrous, isotropic porous material. A porous material having pores or voids precisely controlled, which is called a microfilter membrane, is advantageously used. This microfilter membrane may sometimes be called a membrane filter or defined as a sponge-shaped body. Hereinafter, when embodiments and examples of the present invention are described in further detail with reference to the attached drawings, such porous materials are generically called membrane filters.

As shown in FIG. 1, a solution 13 containing an analyte is dropped as a droplet onto a membrane filter 11 by use of a pipette 12. After that, the solution 13 is dried and the membrane filter 11 is allowed to hold the analyte. The analyte that has been precipitated and held on the membrane filter 11 is denoted by reference numeral 14.

The membrane filter 11 used in the present embodiment has a thin-film-shape and is microscopically a non-fibrous, isotropic porous material. The membrane filter 11 is made of a material containing any of polypropylene, polysulfone, nylon, and polyethersulfone. On the other hand, as comparative examples, membrane filters containing a fibrous structure such as at least one of cellulose, nitrocellulose, cellulose mixed ester, quartz fiber, glass fiber, and polyvinylidene difluoride were used.

FIG. 2 shows an example of an apparatus or method for transmission spectrum measurement using a terahertz wave. As shown in FIG. 2, femtosecond pulse laser light emitted from a mode-lock titanium-sapphire laser (femtosecond laser) 21 is split into two beams by a half mirror and the like, and one beam is condensed and irradiated on a terahertz wave generator 23. As the terahertz wave generator 23, there is used a so-called a photoconductive antenna that is constituted, for example, by a pair of electrodes formed on low-temperature grown gallium arsenide. At this time, a voltage of about 10V is applied to the photoconductive antenna.

The other beam of the two beams of the femtosecond laser light split by the half mirror or the like passes through a delay optical system 22 and is then condensed and irradiated on a terahertz wave detector 24. As the terahertz wave detector 24, a so-called photoconductive antenna that is similar to that of the terahertz wave generator 23 and is constituted by a pair of electrodes formed on low-temperature grown gallium arsenide is used. At this time, a terahertz wave is detected by connecting a high-gain amplifier to the electrodes and amplifying a weak electric current resulting from the terahertz wave.

The terahertz wave 27 emitted from the terahertz wave generator 23 passes through parabolic mirrors 25a, 25b and are condensed and irradiated on a membrane filter 26. The terahertz wave transmitted through the membrane filter 26 is condensed and radiated on the terahertz wave detector 24 by use of parabolic mirrors 25c, 25d, whereby a transmission spectrum of the membrane filter 26 is obtained.

Figure 3A:
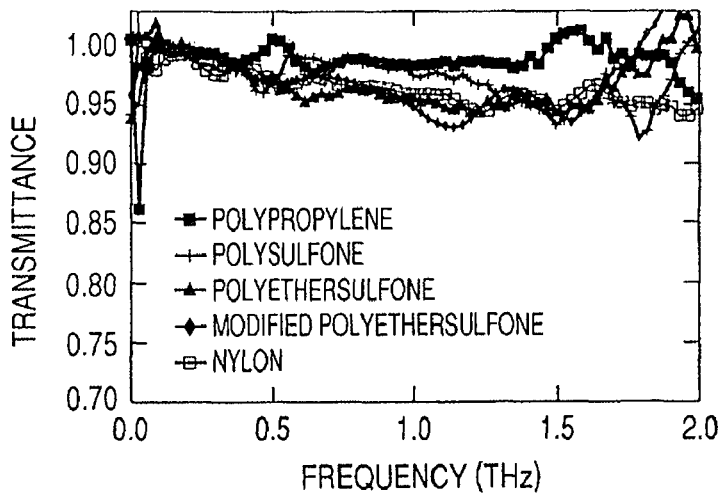
FIGS. 3A, 3B and 3C are graphical representations showing the transmittances of membrane filters made of various kinds of materials with respect to a terahertz wave and an in-plane distribution of the transmittance.

As shown in FIG. 3A, it is seen that in the case of a membrane filter that contains polysulfone as its main component and has a pore diameter of 0.45 μm and a film thickness of 145 μm, the amplitude transmittance is more than 90% in the range of 0.5 THz to 2.0 THz and that the membrane filter is almost transparent in this frequency region. Incidentally, the ordinate of FIG. 3A indicates amplitude transmittance. All of the amplitude transmittance graphs of FIG. 3A show amplitude transmittances when no analyte is present on the membrane filter. It is preferred that membrane filters have a high amplitude transmittance and a constant transmittance when no analyte is present. From FIG. 3A, it is also seen that in the case of any of polypropylene, polyethersulfone, and nylon, the amplitude transmittance is more than 90% in the range of 0.5 THz to 2.0 THz. A membrane filter whose pore diameter is as small as the order of micrometers like this and which is mainly used in biochemistry may sometimes be called a microfilter membrane as described above.

Figure 3B:
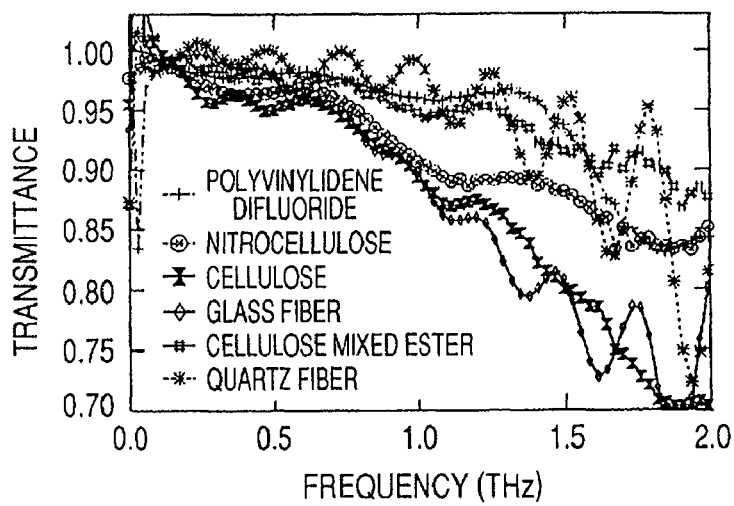

On the other hand, as is seen from FIG. 3B, in the case of polyvinylidene difluoride, nitrocellulose, cellulose, glass fiber, cellulose mixed ester, and quartz fiber, the frequency dependence of amplitude transmittance is great and that the amplitude transmittance may sometimes be less than 90% in the range of 0.5 THz to 2.0 THz.

The above-mentioned materials are studied by introducing the transmittance Abbe number v'. As shown in Table 1 of FIGS. 17A and 17B, the transmittance Abbe number of each of polypropylene, polysulfone, nylon, and polyethersulfone is not less than 20. On the other hand, however, it is seen that the transmittance Abbe number of each of polyvinylidene difluoride, nitrocellulose, cellulose, glass fiber, cellulose mixed ester, and quartz fiber is less than 10. Incidentally, the frequencies of 0.5 to 2.0 THZ were used in the measurement, with the upper limit frequency set at 2.0 THz, the lower limit frequency at 0.5 THz and the middle frequency at 1.0 THz.

That is, in the membrane filters of non-fibrous, isotropic porous materials containing any of polypropylene, polysulfone, nylon and polyethersulfone, the results that the amplitude transmittance is high (not less than 90% at 2.0 THz) and that the frequency dependence of amplitude transmittance is small (transmittance Abbe number of not less than 20) were obtained.

On the other hand, in the membrane filters of cellulose and the like containing a fibrous structure, there were obtained the results that the amplitude transmittance was low (less than 90% at 2.0 THz) and that the frequency dependence of amplitude transmittance was large (transmittance Abbe number of less than 10).

From the experiment facts, it is sees that it is desirable to use the membrane filters formed of non-fibrous, isotropic porous materials containing at least any of polypropylene, polysulfone, nylon, and polyethersulfone rather than the membrane filters of cellulose and the like containing a fibrous structure.

Membrane filters formed of non-fibrous, isotropic porous materials having a high amplitude transmittance in bulk are also considered to be desirable even when these are materials other than polypropylene, polysulfone, nylon, and polyethersulfone. That is, it is estimated that the amplitude transmittance is not less than 90% at 2.0 THz and that the transmittance Abbe number is not less than 20. Accordingly, it is desirable to use membrane filters that are formed of non-fibrous, isotropic porous materials containing, as main components, the above-described desirable resins for which it is known that the amplitude transmittance for terahertz waves is high and that the frequency dependence is small.

Figure 10:
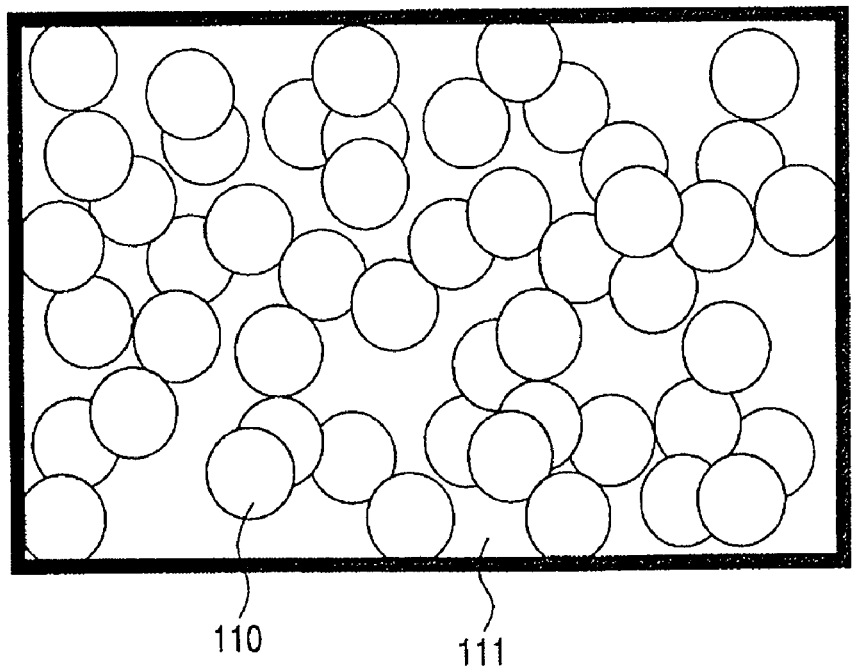
FIG. 10 is a diagram illustrating a porous material formed of a particulate structure.
Figure 11:
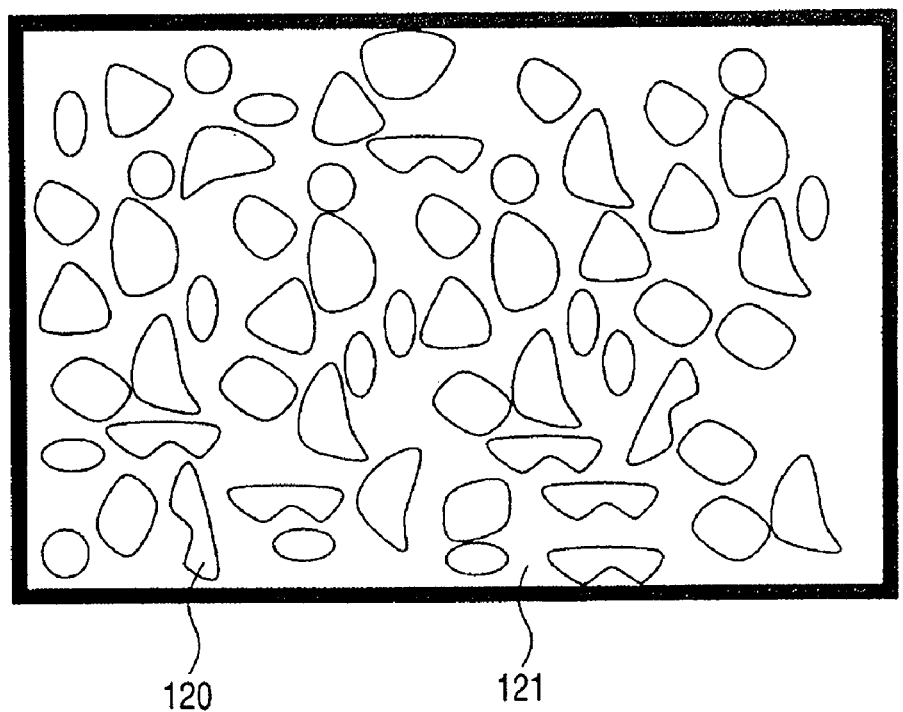
FIG. 11 is a diagram illustrating a porous material formed of a sponge-shaped structure.
Figure 12:
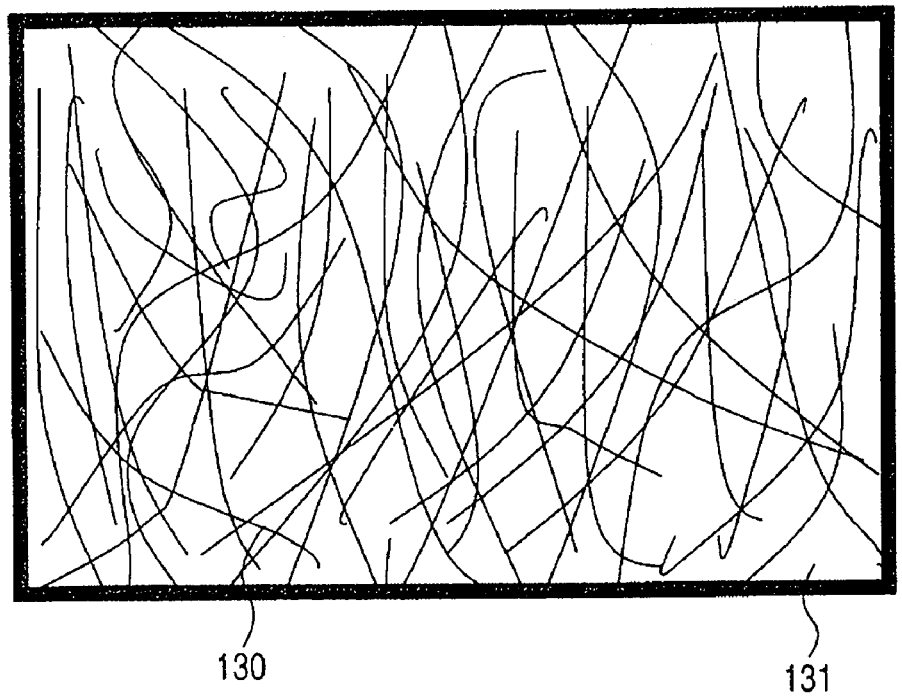
FIG. 12 is a diagram illustrating a porous material formed of a fibrous structure.
Figure 13:
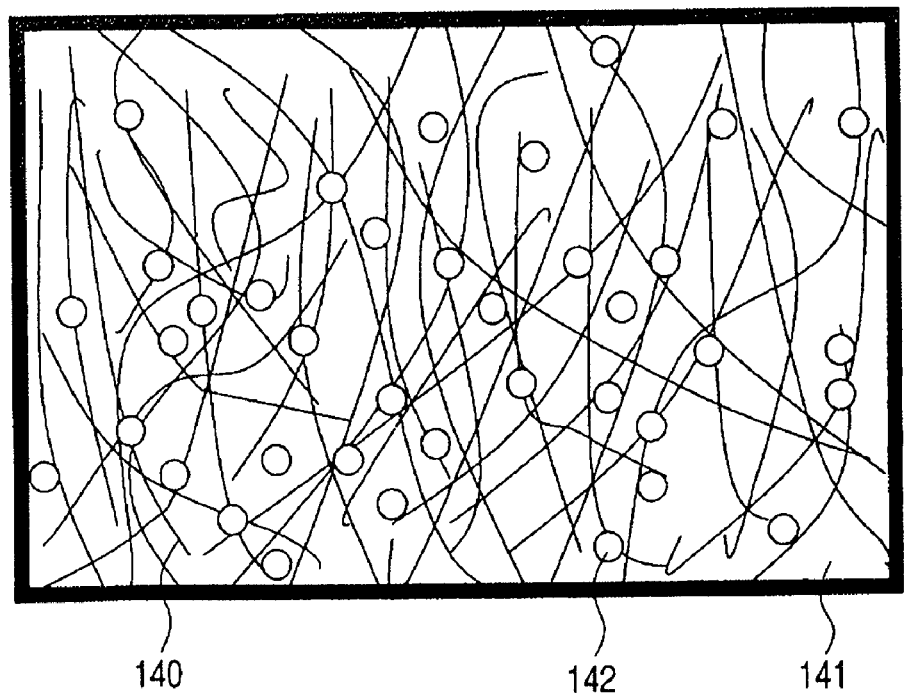
FIG. 13 is a diagram illustrating a porous material including a fibrous structure.
Figure 14:
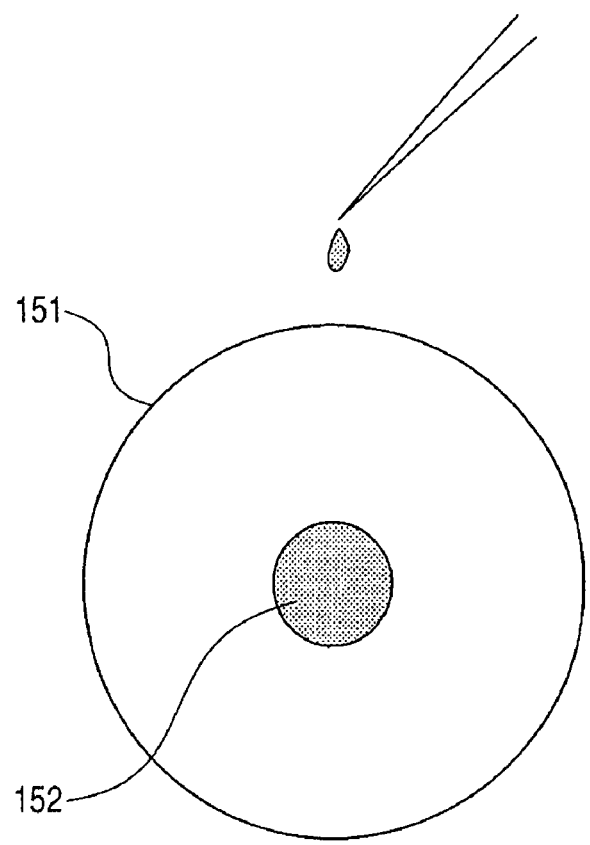
FIG. 14 is a diagram illustrating a state in which a liquid analyte permeates a membrane filter and is held thereby uniformly.
Figure 15:
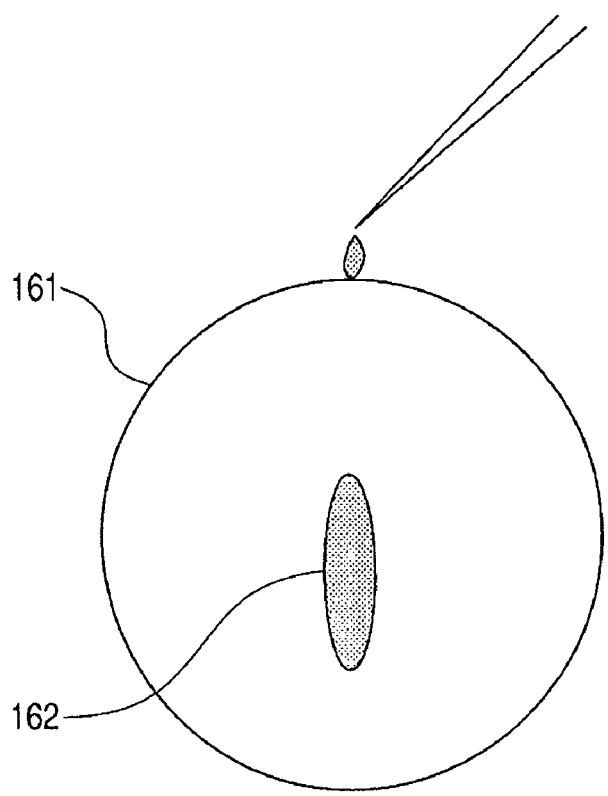
FIG. 15 is a diagram illustrating a state in which a liquid analyte permeates a membrane filter and is held thereby non-uniformly.

When a liquid analyte is allowed to drop as a droplet onto a membrane filter, in a case where the membrane filter is formed of a particulate structure as shown in FIG. 10 or sponge-shaped structure as shown in FIG. 11, the liquid analyte is uniformly distributed as shown in FIG. 14. However, it has been seen that in membrane filters containing a fibrous structure 130, 140 such as shown in FIGS. 12 and 13, the distribution is nonuniform as shown in FIG. 15. As described above, in a state in which a liquid analyte is nonuniformly distributed, spatial nonuniformity occurs in the electromagnetic field distribution of a transmitted terahertz wave and adverse noise signals may sometimes be generated when the time waveform of the transmitted terahertz waves is Fourier transformed. Also from this viewpoint, it is desirable to use membrane filters formed of non-fibrous, isotropic porous materials.

Of the materials listed in Table 1 of FIGS. 17A and 17B, polypropylene, polysulfone, polyethersulfone, and nylon have structures formed of a non-fibrous, isotropic porous material and the liquid analyte was uniformly distributed in membrane filters formed of these materials.

All the experiment facts considered, a comparison between the membrane filters formed of structures of a non-fibrous, isotropic porous material including polypropylene, polysulfone, nylon, and polyethersulfone and the membrane filters containing a fibrous structure has revealed the following. The former group of materials is excellent in all of the three items of amplitude transmittance, the degree of constancy of amplitude transmittance, and the uniformity of the analyte distribution, and the conclusion has been reached that these membrane filters are desirable as analyte holding means made available for use in spectrometry using a terahertz wave. Furthermore, it is considered that membrane filters formed of a structure of a non-fibrous, isotropic porous material other than the above-mentioned polypropylene, polysulfone, nylon, and polyethersulfone are also desirable as the analyte holding member so long as the amplitude transmittance in bulk is high.

In the above-described membrane filters, it is necessary that the average pore diameter of a porous material be not more than the wavelength of a terahertz wave in order to avoid the scattering of the terahertz wave, and if the average pore diameter is sufficiently smaller than the wavelength, then the avoidance of the scattering will be improved in proportion thereto. For example, in general, when a scatterer having the same size as the wavelength of an electromagnetic wave is present, the effect of Mie scattering becomes dominant and the electromagnetic wave attenuates rapidly. When a scatterer having a size that is 1/10 of the wavelength of an electromagnetic wave is present, the effect of Rayleigh scattering becomes dominant and the electromagnetic wave attenuates rapidly also in this case. For this reason, it becomes difficult to detect the electromagnetic wave after the transmission through an analyte. If the average pore diameter of the above-described membrane filters is not more than the above-described sizes, the effect of scattering is reduced more and the porous materials behave as uniform solids for an electromagnetic wave. From the forgoing, it is desirable that the average pore diameter of a porous material be not more than the wavelength of an electromagnetic wave used, although the attenuation of the electromagnetic wave is brought about to some extent in the above-described two cases.

Therefore, for example, membrane filters formed of porous materials having average pore diameters of about 0.1 μm to 2.0 μm can be mentioned as preferred examples. Membrane filters including a scatterer whose average pore diameter is about 0.1 μm to 2.0 μm behave as uniform bodies for a terahertz wave.

Examples of a method of holding an analyte on the above-described membrane filters include a method that involves allowing a liquid having an analyte dissolved or dispersed therein to drop as a droplet onto the membrane filter, followed by drying. Alternatively, there is included a method that involves allowing a gas containing an analyte to permeate the above-described membrane filter and allowing the analyte to be adsorbed by the membrane filter and held thereby.

By using a membrane filter as described above as a carrier of an analyte, the flatness of the surface and the uniformity of thickness are ensured and the analyte can be held easily, with the result that scattering and other phenomena can be suppressed. Therefore, this increases the reliability, stability and ease of the measurement of a change in the propagation state of a terahertz wave, and by extension, the accuracy of inspection and analysis results. Also, when an analyte such as a living organism is measured, the analyte can be appropriately entangled with the pores of a membrane filter material to make it easy to hold the analyte. Therefore, even when the analyte is dried, it becomes easy to hold the analyte while maintaining the three-dimensional construction of the analyte and the accuracy of measurement can be increased. Also, the facts that the amplitude transmittance of the membrane filter is close to 1 and that the thickness of the membrane filter is smaller than the order of magnitude of the wavelength of a terahertz wave used are effective in suppressing multiple reflection.

Examples of the measurement of a change in the propagation state of a terahertz wave irradiated to an analyte held by the membrane filter include the measurement of a transmission spectrum and a reflection spectrum which is an intensity change corresponding to the wavelength of a terahertz wave. Alternatively, the measurement of an intensity change according to time lapse of a terahertz wave is also included.

By making a comparison between a transmission or reflection spectrum by a terahertz wave of the membrane filter not including an analyte and a spectrum of the membrane filter including an analyte, a transmission or reflection spectrum having the effect of the membrane filter excluded therefrom can be obtained.

Figure 3C:
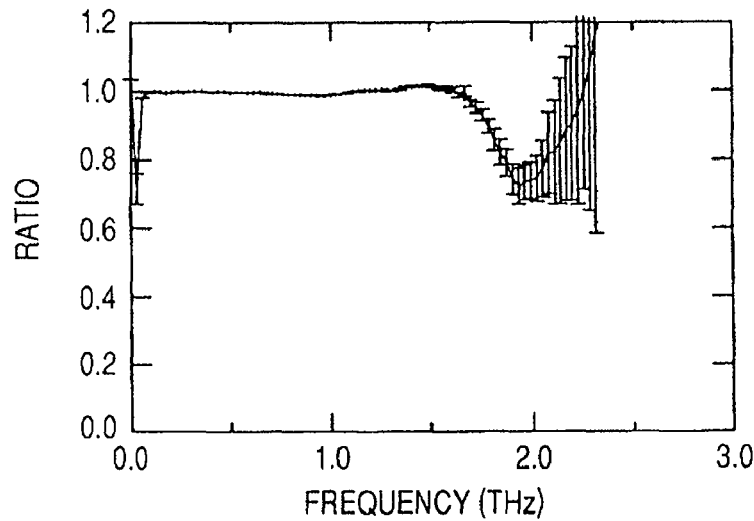

In this connection, the ratio of amplitudes of a transmitted terahertz wave between two different points in the membrane filter is shown in FIG. 3C. The abscissa of FIG. 3C indicates frequency and the ordinate indicates the ratio of amplitude transmittances. As shown in FIG. 3C, the amplitude ratio is approximately 1.0 in the range of 0.1 THz to 1.5 THz, and it is seen that in this frequency region the membrane filter has a very small in-plane distribution of amplitude transmittance. Incidentally, frequencies of not more than 0.1 THz and of not less than 1.5 THz were outside the effective sensitivity range of the measuring apparatus used in this experiment. However, for this band, analyses of frequencies of not less than 1.5 THz are possible if a measuring apparatus of a wider band is used. From the foregoing, it is seen that also in obtaining reference wave data of the membrane filter not containing an analyte, the membrane filter is desirable.

Incidentally, the analysis method of the present invention can be advantageously used in DNA, RNA, proteins, sugars, nucleic acid bases, compounds containing nucleic acid bases, amino acids and the like as biomolecules. For use in the analyses of DNA and RNA, it is advisable to use modified polyethersulfone that is negatively charged of the membrane filters listed in Table 1 of FIGS. 17A and 17B. The reason is that because the amplitude transmittance and the transmittance Abbe number are high, and because modified polyethersulfone is negatively charged, the membrane filter captures DNA and RNA with good efficiency.

Returning to the description with reference to the drawings, a membrane filter 11 is allowed to hold the analyte 14 by the method shown in FIG. 1 and after that, a membrane filter 26 that holds the analyte is measured with a terahertz wave by the measuring method or apparatus shown in FIG. 2, whereby a transmission spectrum and the like are obtained.

Although in this embodiment a femtosecond laser and a photoconductive antenna are used in the generation means and detection means of a terahertz wave, the generation means and detection means are not limited thereto. For example, a terahertz wave that is generated when femtosecond pulse laser light is radiated to an indium arsenide substrate may also be used.

Further, although the so-called THz time domain spectroscopy is used in this embodiment, the method of terahertz spectroscopy is not limited thereto. For example, for the terahertz wave generation, it is also possible to use a tunable single-frequency terahertz light source, such as so-called terahertz parametric oscillation to which the nonlinear optical effect is applied and a GaP (gallium phosphide) Raman terahertz wave generator. Further, for the detection, it is possible to use a spectroscopic method that involves measuring the wavelength dependency of transmitted terahertz wave intensity by use of a Si bolometer that uses liquid helium. In addition, Fourier transform infrared (FTIR) spectroscopy may also be used.

The analyte that is an object of inspection is not limited to a substance that is soluble in water and a substance that is not soluble in water (or other liquids) may also be used. For example, it is also possible to adopt a method that involves allowing resin fine particles to be dispersed in a liquid, dropping the dispersion as a droplet onto a membrane filter, removing the liquid by drying or other means, and then performing the analysis (detection, identification and the like) of an aggregate of the remaining resin fine particles together with the membrane filter by use of a terahertz wave.

In the application of an analyte, a method can also be used in which a chargeable membrane filter is used and the molecules of the analyte are adsorbed by an electrostatic force, such as the electrospray method.

Next, more concrete examples will be described.

EXAMPLE 1

Example 1 will be described. In this example, an aqueous solution of glucose is dropped as a droplet onto a membrane filter by using a pipette. After that, the filter is dried for approximately 20 hours to form a precipitate of the aqueous solution of glucose on the membrane filter. For example, the concentration of the aqueous solution of glucose is about 250 g/l, and the amount of the dropped liquid droplet that is about 20 μl.

The membrane filter used here is, for example, a membrane filter manufactured by Nihon Pall Ltd. (product No. 80574; material: modified nylon; pore diameter: 0.8 μm).

The membrane filter that holds the precipitate of the aqueous solution of glucose is disposed in the position of the membrane filter 26 in FIG. 2. The terahertz wave is condensed and irradiated to the precipitate of the aqueous solution of glucose that is held by the membrane filter.

Figure 4:
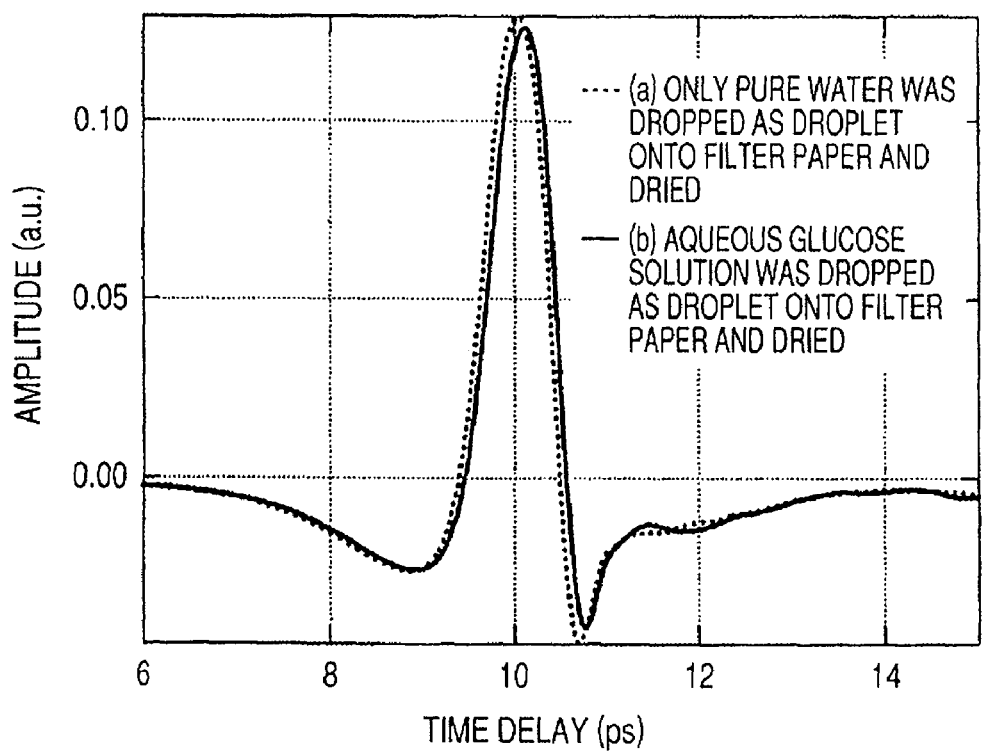
FIG. 4 is a graphical representation showing a time waveform of a terahertz wave.

The time waveform of the terahertz wave transmitted through the precipitate of the aqueous solution of glucose is obtained by moving the delay optical system 22. An example of the thus obtained time waveform is indicated by the solid line (b) of FIG. 4. On the other hand, for comparison, the same amount of pure water as that of the aqueous solution of glucose is dropped as a droplet on another membrane filter, and after drying for about 20 hours, the time waveform of the transmitted terahertz wave is measured. An example of the thus obtained time waveform is indicated by the dotted line (a) of FIG. 4. In FIG. 4, the abscissa indicates time (the unit is picosecond ps) and the ordinate indicates the relative magnitude of the amplitude of the terahertz wave.

The obtained time waveform of the terahertz wave is Fourier transformed, the amplitude and phase of the terahertz wave in the frequency region are calculated, and the complex refractive index is determined for the precipitate of the aqueous solution of glucose by using the equation as described in Japanese Patent Application Laid-Open No. 2002-5828.

Figure 5:
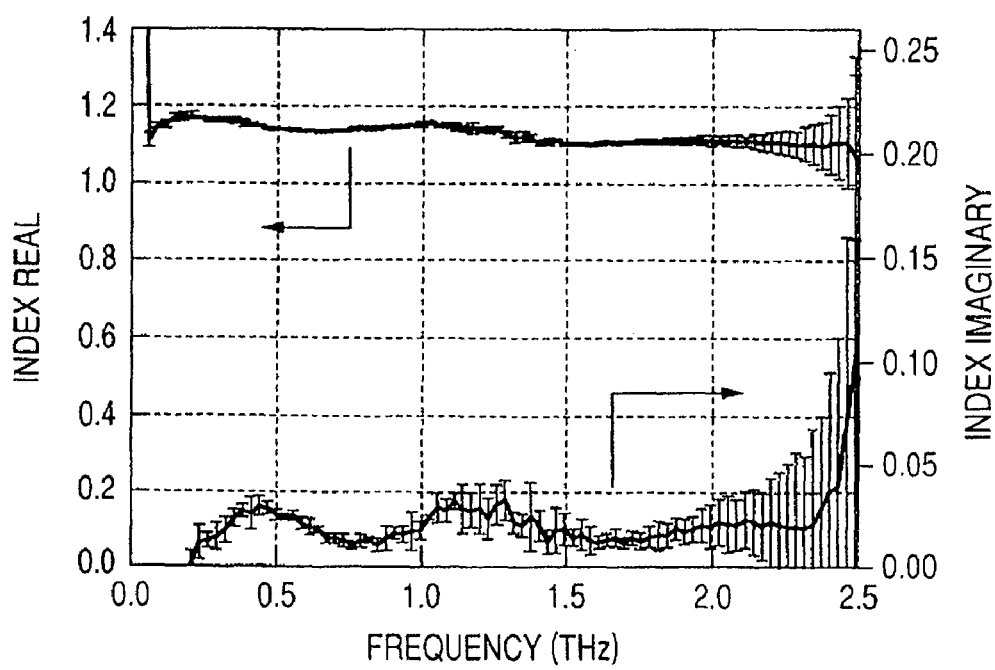
FIG. 5 is a graphical representation showing complex refractive index.

FIG. 5 is a graph of a real part and an imaginary part of the obtained complex refractive index of the aqueous solution of glucose. In the graph, the membrane filter thickness was used as the sample thickness necessary for calculating the complex refractive index. Strictly, the thickness of the precipitated glucose should be used. However, because it is difficult to measure the thickness of the glucose in the membrane filter, the calculation was made by using the thickness of the membrane filter as the sample thickness on a trial basis. It is possible to know the kind and amount of an analyte by checking the calculation results against data on the complex refractive indexes of various materials previously obtained and stored.

Thus, it is possible to analyze substances or to obtain information thereon without the need of allowing the membrane filter to carry a reagent. Further, since the membrane filter has almost the same thickness as the wavelength of the terahertz wave used and has a small refractive index, the multiple reflection inside the membrane filter is suppressed very well, which is advantageous for spectrum analyses. This is because when multiple reflection is observed, it is necessary to perform numerical calculations to remove the effect of the multiple reflection in a data processing step, which requires additional labor. Furthermore, when the multiple reflection cannot be removed, detrimental effects such as lowering in the effective wavelength resolving power may occur.

EXAMPLE 2

Figure 6:
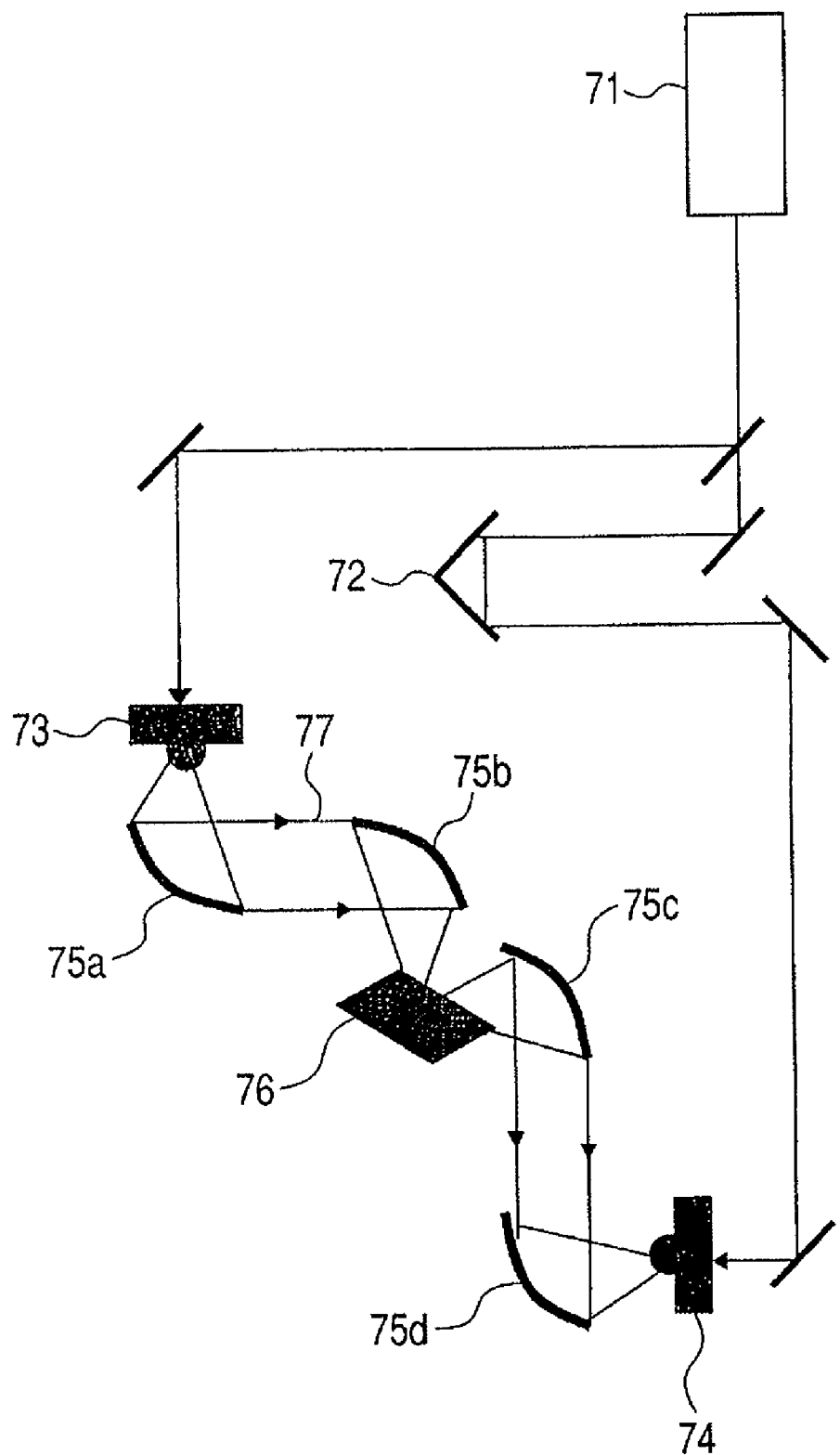
FIG. 6 is a diagram illustrating an optical arrangement for reflection spectroscopy for performing material analysis with a terahertz wave.

Example 2 will be described. In Example 2, as shown in FIG. 6, femtosecond pulse laser light emitted from a mode-lock titanium-sapphire laser (femtosecond laser) 71 is split into two beams by a half mirror and the like, and one bean is condensed and irradiated on a terahertz wave generator 73. A so-called photoconductive antenna that is constituted, for example, by a pair of electrodes formed on low-temperature grown gallium arsenide is used as the terahertz wave generator 73. At this time, a voltage of about 10V is applied to the photoconductive antenna.

The other beam of the femtosecond laser light split by the half mirror and the like passes through a delay optical system 72 and is then condensed and irradiated on a terahertz wave detector 74. A so-called photoconductive antenna that is similar to the terahertz wave generator 73 and is constituted by a pair of electrodes formed on low-temperature grown gallium arsenide is used as the terahertz wave detector 74. At this time, the terahertz wave is detected by connecting a high-gain amplifier to the electrodes and amplifying a weak electric current resulting from the terahertz wave.

The terahertz wave 77 emitted from the terahertz wave generator 73 pass through parabolic mirrors 75a, 75b and are condensed and irradiated on a membrane filter 76. The terahertz wave that has been reflected by the membrane filter 76 is condensed and irradiated on the terahertz wave detector 74 by use of parabolic mirrors 75c, 75d, whereby a reflection spectrum of the membrane filter 76 is obtained.

By obtaining a reflection spectrum in this manner, the complex refractive index of an analyte can also be determined. In order to increase the reflectance, a metal film or a metal sheet of aluminum or the like may be applied to the rear side of the membrane filter 76.

EXAMPLE 3

Figure 7:
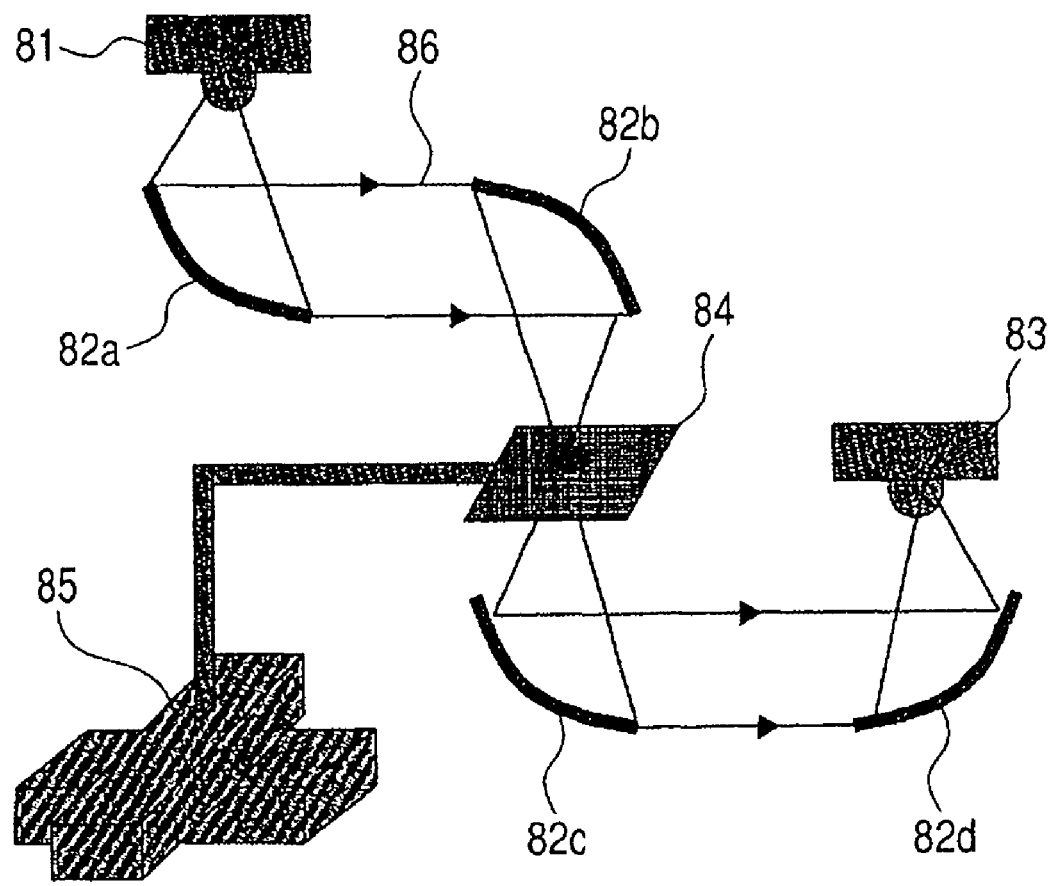
FIG. 7 is a diagram illustrating a configuration in which a membrane filter is provided on a mechanical XY stage.

Example 3 will be described. In Example 3, as shown in FIG. 7, there is provided a mechanical XY stage 85 for driving, in a horizontal biaxial direction, a membrane filter 84 having an analyte dropped thereon. A terahertz wave 86 emitted from a terahertz wave generator 81 pass through parabolic mirrors 82a, 82b and are condensed and irradiated on the membrane filter 84.

The terahertz wave transmitted through the membrane filter 84 is condensed and irradiated on a terahertz wave detector 83 by use of parabolic mirrors 82c, 82d, whereby a transmission spectrum of the membrane filter 84 is obtained. At this time, when the analyte dropped onto the membrane filter 84 is dried, there are cases where it is difficult to visually observe the position of the analyte on the membrane filter 84. Therefore, by using the mechanical XY stage 85, the membrane filter 84 including the analyte is driven in a direction substantially perpendicular to the travel direction of the terahertz waves 86.

On the membrane filter 84, there is a change in the intensity and delay time of the transmitted terahertz wave between a position where a dried analyte is present and a position where dried analyte is not present. At this time, by plotting the measured intensities or the like of the transmitted terahertz wave, an image of the transmitted terahertz wave for the membrane filter 84 is obtained. The position of the analyte on the membrane filter 84 is accurately seen based on the terahertz wave image of the membrane filter 84, whereby the terahertz spectrometry of the analyte can be accurately performed. In this case, it is also possible to drop a plurality of analytes as droplets at different locations on the same membrane filter and to measure these analytes.

Figure 8:
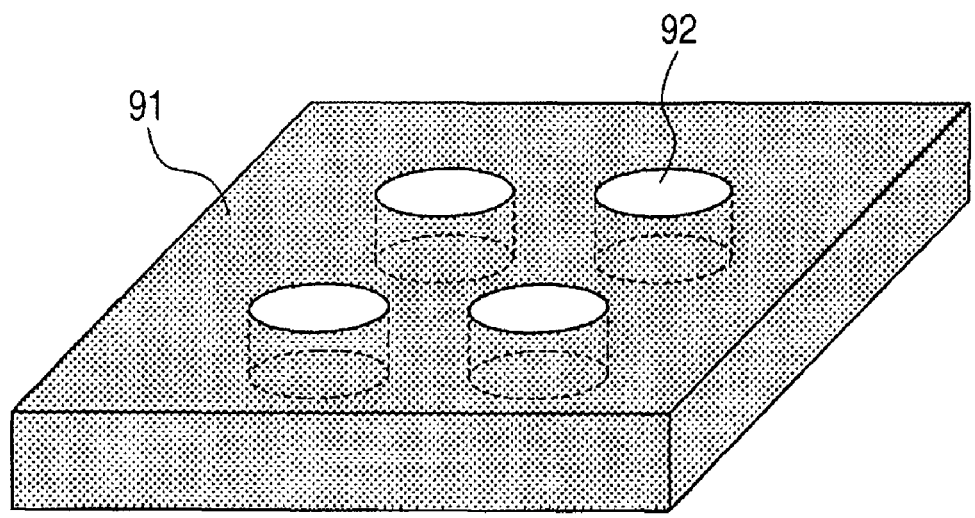
FIG. 8 is a perspective view illustrating an example in which membrane filters are provided on a member having a plurality of wells.

For example, it is possible to adopt an arrangement such that a membrane filter is provided in each of a plurality of wells 92 having a partition wall, which are formed in a support 91 (made of resin, metal or the like) as shown in FIG. 8 and the support 91 is moved by using a mechanical XY stage, whereby a plurality of analytes are measured at a time. In order to avoid the scattering and the like of a terahertz wave, it is preferred that the diameter of the well 92 be several millimeters to about 10 mm.

Figure 9:
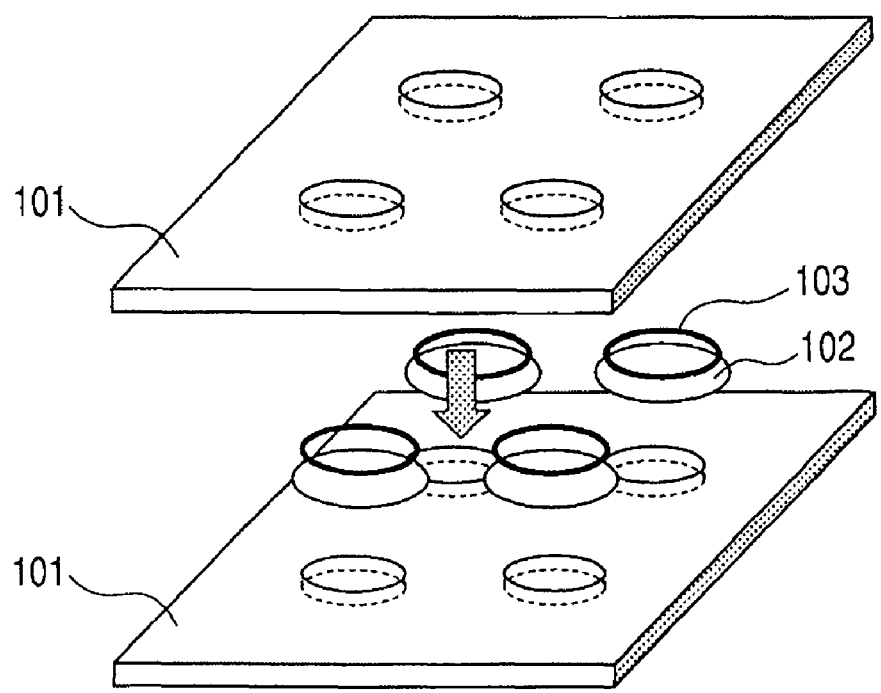
FIG. 9 is a perspective view illustrating the details of an example of the member of FIG. 8.

FIG. 9 shows an example of the support in which a membrane filter 102 is sandwiched with two resin sheets 101 each having wells that are cylindrical through-holes to form a one-piece structure. At this time, by stretching the membrane filter 102 so as not to generate bending, wrinkling or the like, the scattering or reflection in an undesired direction of a terahertz wave can be prevented. Further, in order to prevent the mixing of samples of the wells, the resin sheets 101 and the membrane filters 102 may be thermocompressed to each other, or O-rings 103 may be disposed around the respective wells. The O-rings 103 are used when the membrane filter 102 is sandwiched by the resin sheets 101. It is desirable that the membrane filter 102 is one size larger than the well.

Moreover, in order to remove unnecessary transmittance of a terahertz wave through the resin sheets 101, either or both of the resin sheets 101 may be replaced with metal sheet(s) of aluminum or the like. If this arrangement is adopted, there is obtained an analyte holding member for holding an analyte from which information is to be obtained, which includes a partition wall that holds the analyte in a specific region and a porous material within the partition wall and has, in a region other than the region constituted by the partition wall, at least a member which does not transmit an electromagnetic wave.

In this case, the well plays also the role of a diaphragm of a terahertz wave. Furthermore, in the configurations shown in FIGS. 8 and 9, in consideration of the fact that the support 91 and the resin sheet 101, which are to be moved, cannot be designed to be so large, it is possible to take measures as described blow in order to positively prevent an unnecessary terahertz wave from entering the detector. That is, above or blow the support 91 or the resin sheet 101 or in both places, there is provided a mask (made of metal, for example) having an opening of an appropriate shape that is aligned with respect to the well that becomes an object of measurement and the travel direction of the terahertz wave. If this arrangement is adopted, an unnecessary terahertz wave is more surely shut off by the mask and a necessary terahertz wave is guided through the mask opening, with the result that measurement with better accuracy can be performed.

Also, by dropping an analyte as a droplet into each of the multiple wells such as described above and changing the relative positional relationship between the wells and the terahertz wave, the multiple analytes can be measured at a high speed. In this case, the analyte is not dropped into one of the wells and that well is not allowed to hold any analyte, or only a solvent used for dissolving the analyte is dropped as a droplet into one of the wells. This one well serves as a reference well, and a reciprocating motion is repeated a plurality of times between the reference well and the wells having the analyte dropped therein, and the difference between a change in propagation state of the terahertz wave at the reference well and that at another well is measured a plurality of times and averaged. This permits high-accuracy measurements.

EXAMPLE 4

Example 4 will be described. In Example 4, an aqueous solution of DNA is dropped as a droplet onto a membrane filter. For example, the concentration of 5.4 kb of a vector pcDNA3 aqueous solution is 10 μg/μl and the amount of the aqueous DNA solution is 5 μl. A membrane filter having a pore diameter of about 0.45 μm and a thickness of about 127 μm, the main component of which is hydrophilic nylon, (for example, a membrane filter manufacture by Nihon Pall Ltd., product No. 66607) is used as the membrane filter of this example. The aqueous solution of DNA may be dropped as a plurality of droplets in the same place of the membrane filter to raise the concentration of the solution.

Then, the membrane filter having the aqueous DNA solution dropped thereon is dried at room temperature. The dried membrane filter is subjected to terahertz wave spectrometry by the method described in Example 1 and a transmittance spectrum is measured. By checking the measurement results against a DNA data base of terahertz wave spectrometry (transmittance or reflectance spectrum) previously obtained and stored, it is possible to obtain information on the DNA (for example, whether the DNA is single stranded or double stranded, approximate estimate of the length of a base pair, etc.). Thus, it is seen that according to the analysis method of the present invention, by allowing a porous material to hold a solution or lysate of biomolecules and then performing drying, information on an analyte can be obtained.

Besides the method of supplying an analyte by dropping as a droplet as described above, it is also effective to adopt a method that involves applying a solute to a chargeable membrane filter by using an electrostatic force of attraction according to the electrospray method or the like. In this case, it is possible to allow the well structure described in Example 1 above to function as a mask for selective application without modification. Incidentally, it is advisable that on an appropriate surface of the membrane filter, a structure with which an electrode for moving a charge comes into contact be provided in order to maintain the electrostatic force of attraction.

By cutting off a portion of the membrane filter onto which the DNA has been dropped as a droplet and immersing the portion in about 10 ml of pure water, the DNA held by the membrane filter can be recovered. The membrane filter has the characteristics such that it maintains the structure of the held DNA even after drying and can elute the DNA again by being immersed in pure water. In this manner, biomolecules are eluted from the porous material after the acquisition of information on an analyte, whereby biomolecules can be reused.

In this example, DNA analyses and the like can be performed in a label-free manner and it is possible to take out again a DNA used in an inspection and to use the DNA in another inspection. In this example, a membrane filter whose main component is modified polyethersulfone may be used.

EXAMPLE 5

Example 5 of the present invention will be described below. In this example, first, an aqueous solution of avidin (concentration: about 0.1 μg/μl) is dropped as a droplet onto a membrane filter. A membrane filter having a pore diameter of about 0.45 μm and a thickness of about 127 μm, the main component of which is hydrophilic nylon, (for example, a membrane filter made by Nihon Pall Ltd., product No. 66607) is used as the membrane filter of this example. The aqueous solution of avidin may be dropped as a plurality of droplets in the same place of the membrane filter to raise the concentration of the solution.

The membrane filter having the aqueous avidin solution dropped thereon is dried at room temperature. The dried membrane filter is subjected to terahertz wave spectrometry by the method described in Example 1 and a transmittance spectrum is obtained.

Subsequently, an aqueous solution of biotin is dropped as a droplet onto the place on the membrane filter where the aqueous solution of avidin has been dropped. Because the membrane filter has the characteristics of maintaining the activity of avidin even after the drying of the membrane filter, the avidin held on the membrane filter initiates an antigen-antibody reaction with the biotin in the aqueous solution of biotin and combines with the biotin.

After drying the membrane filter having the aqueous biotin solution dropped thereon, the membrane filter with the reaction product is again subjected to terahertz wave spectrometry by the method described in Example 1, whereby an amplitude-transmittance spectrum is obtained. By checking this spectrum against a data base on the antigen-antibody reaction of avidin and biotin (for example, amplitude transmittance spectrum) previously obtained and accumulated, it is possible to measure, for example, to which extent the antigen-antibody reaction has occurred.

EXAMPLE 6

Example 6 of the present invention will be described below. In this example, 30 µl of an aqueous solution of bovine serum albumin (BSA) (concentration: 20 mg/ml) is dropped as a droplet onto a membrane filter. A membrane filter made of a non-fibrous, isotropic porous material having a pore diameter of 0.45 µm and a thickness of about 140 µm, the main component of which is hydrophilic polyethersulfone, is used as the membrane filter of this example. Subsequently, the aqueous solution of BSA is heated in a hot bath at 72° C. to 75° C. for 3 minutes to be denatured. The same amount of the denatured aqueous solution of BSA is dropped as a droplet in another place of the membrane filter.

Figure 16:
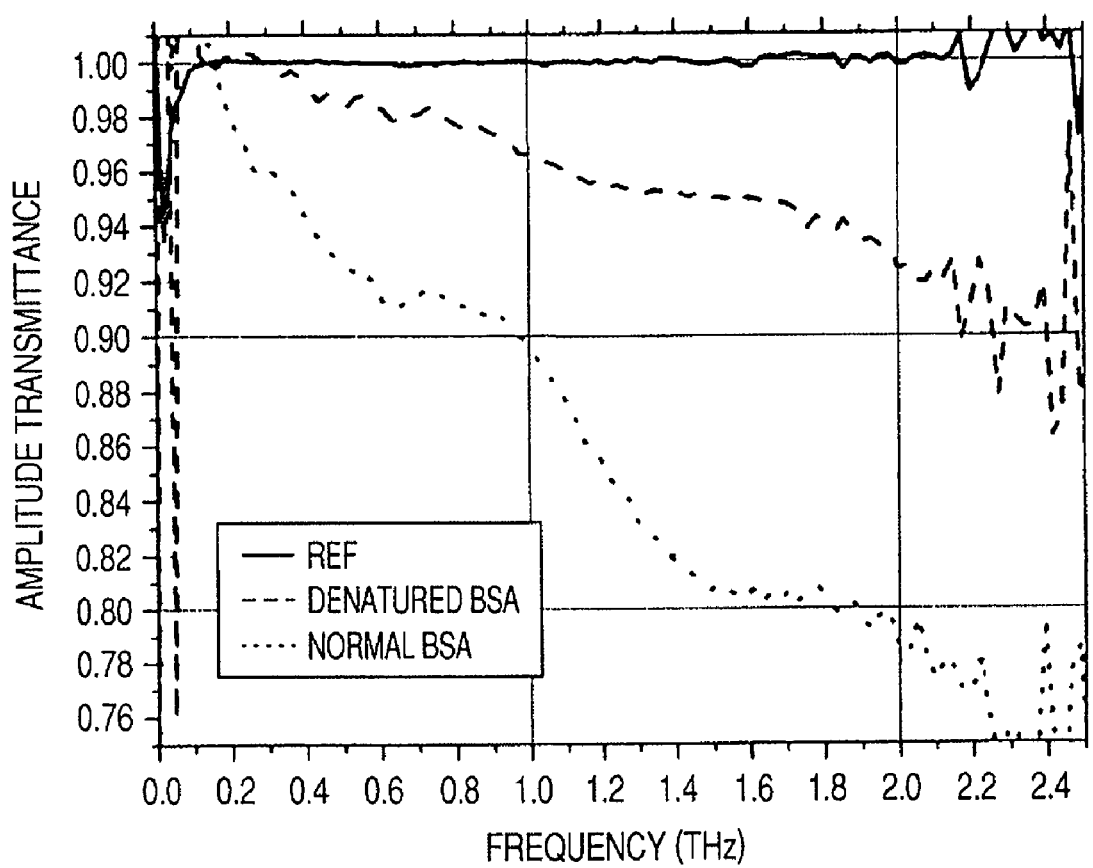
FIG. 16 is a graphical representation illustrating a comparison of amplitude transmittances of denatured molecule and normal molecule of BSA.

The membrane filter having the aqueous BSA solution and the denatured aqueous BSA solution dropped thereon are dried under the condition of 4° C., and after that, the precipitates, along with the membrane filter, are again subjected to terahertz wave spectrometry by the method described in Example 1, whereby amplitude transmittance spectra are obtained. Results of a comparison between the amplitude transmittance of the BSA and the amplitude transmittance of the denatured BSA are shown in FIG. 16. In FIG. 16, "REF" indicates the ratio of amplitude transmittances at the same point on the membrane filter (measured twice at the same point), and serves as a measure for the fluctuation of signals and the reliability interval of the whole experiment system.

In FIG. 16, "normal" and "denatured" respectively indicate the amplitude transmittance of the aqueous solution of normal BSA and that of the aqueous solution of thermally denatured BSA. From this it is seen that whether the denaturation of BSA that is protein occurs can be measured. This difference in amplitude transmittance suggests that the three-dimensional structure of BSA has changed. In this example, it could be confirmed that the amplitude transmittance of the denatured BSA increases greatly.

EXAMPLE 7

Figure 18:
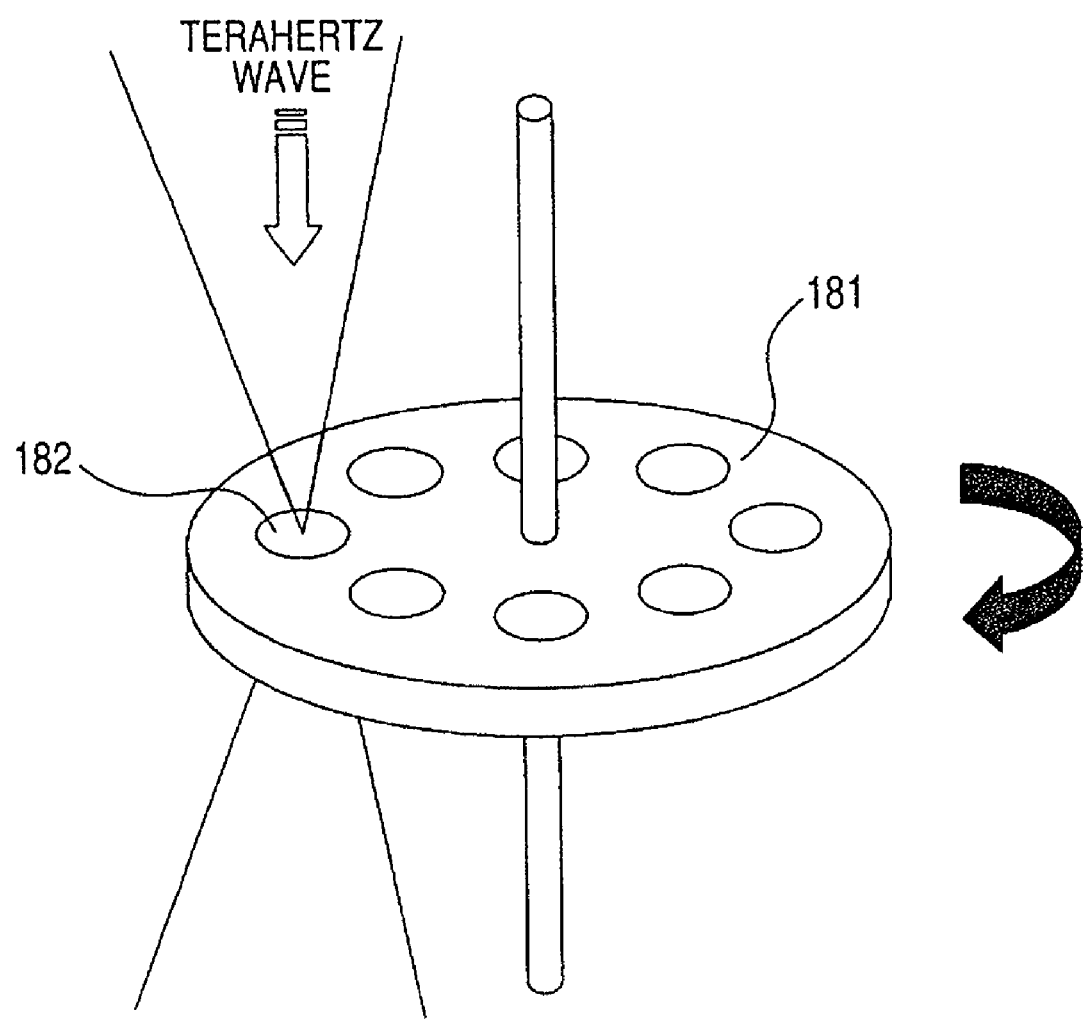
FIG. 18 is a diagram illustrating an example of a membrane filter provided on a rotary disk.

Example 7 of the present invention will be described. In this embodiment, as shown in FIG. 18, wells which can transmit a terahertz wave are provided in eight places of a disk 181 that is rotatable about a central axis, and a membrane filter 182 is provided in each of the wells. The wells are provided at locations radially apart by the same distance from the center of the rotation on the disk 181. An analyte (for example, an aqueous solution of normal BSA) is dropped as a droplet onto at least one of the membrane filters and the same amount of pure water is dropped as a droplet on another membrane filter as a reference, followed by drying. A terahertz wave is generated by the same method described in Example 1, and the terahertz wave transmitted through each of the membrane filters is detected by a detector. Further, by rotating the disk 181, the analytes held by the eight membrane filters are sequentially brought into a detection position and measured.

Incidentally, at this time, when condensing a terahertz wave on the membrane filter 182 in the well, there are cases where stray light of the terahertz wave may detour around a membrane holding the well (in this example, the disk 181) and reach the detector. Particularly, in a case of low-frequency (for example, 50 GHz or less) components, the effect of the diffraction is great because of their long wavelengths, so that stray light is apt to be generated. However, when the wells are provided at equiangular intervals on the same concentric circle of the disk-shaped member as in this example, the relative positional relationship between the disk-shaped member and the terahertz wave propagating in the space does not change even if the disk is rotated. For this reason, the intensity of stray light that reaches the detector is not so great and scarcely changes. Therefore, by using the method of this example, the number of diaphragms to remove stray light can be reduced or it becomes unnecessary to use diaphragms.

In contrast to this, in Example 3 above, the situation is as follows. In Example 3, as shown in FIGS. 8 and 9, examples in which wells in the number of 2×2 are provided in a rectangular member were described. However, an example where wells in the number of, for example, 3×3 are provided to measure more analytes at a time is considered. In this case, the difference in the intensity of stray light reaching the detector becomes relatively great between the measurement at wells present near the ends of the rectangular member and the measurement at wells present in the central part of the rectangular member. This is because the spatial distribution of the terahertz wave (including stray light and components incapable of being sufficiently condensed) propagating in the space and the relative positional relationship between the holding member and the plurality of wells change depending on the location of a well at which measurement is performed. In a state in which an analyte is not dropped on membrane filters in the wells, it is preferred that the same signal be obtained by measuring at the well in any location on the rectangular member. However, because as described above the intensity of stray light reaching the detector changes when the rectangular member is moved back and forth, right and left, the same signal may sometimes not be obtained. In order to more surely avoid this, in Example 3, the example in which diaphragms (masks having an opening) to remove stray light are appropriately disposed at various places was described.

In this example, it is preferred that the wells disposed in the disk-shaped member be disposed at equiangular intervals around the center of rotation and provide rotational symmetry. This is because rotational symmetry like this ensures that the effect of the stray light of the terahertz wave transmitted through the wells other than the well being measured does not change irrespective of which well is to be measured. Although eight wells are provided in this example, the number of wells is not limited to eight.

Incidentally, if a mechanism is further provided which occludes the wells other than the well being measured, the arrangement of the wells is not limited to the form of rotational symmetry in which the wells are disposed at equiangular intervals. The wells are not necessarily be disposed at equiangular intervals so long as they are provided at locations radially apart by the same distance from the center of the rotation and the rotary member takes the same outer shape in each of the rotary measurement positions. Although in this Example 7 a disk-shaped member is taken as an example as a preferred one, any rotary member may be used so long as it has the same outer shape in each of the rotary measurement positions. For example, the rotary member may have a regular polygonal shape. However, it is necessary that the wells be appropriately disposed at the same radial distance from the rotation center of the rotary member such that the rotary member always takes the same outer shape when each well comes to the measurement position. Although in this Example 7 the rotary member is disposed perpendicularly to the travel direction of a terahertz wave, the arrangement of the rotary member is not limited to this perpendicular arrangement. It is necessary only that the rotary member be disposed so as to be rotatable about the center in a plane which is not parallel to the travel direction of the terahertz wave. In summary, in this example, it is necessary only that the arrangement including the case where a mechanism is provided which occludes the wells other than the well being measured satisfy the following conditions. A plurality of porous materials at least one of which holds an analyte are disposed on a rotary member rotatable about a center in a plane not parallel to the travel direction of an electromagnetic wave, at locations radially apart by the same distance from the center. Further, when the porous materials are sequentially brought into a detection position by rotating the rotary member, the rotary member takes always the same outer shape.

The following effect is obtained by making measurements by the method of this example that uses the configuration described above. The stray light component when measuring a reference signal (terahertz waveform and its Fourier spectrum) of a membrane filter onto which nothing is dropped (or only pure water is dropped as a droplet and dried) and the stray light component contained in a signal generated when measuring a well into which an analyte is dropped as a droplet and dried become identical to each other. Therefore, by performing division between the reference signal and the signal of analyte measurement, stray light components can be easily removed and more accurate measurements become possible.

EXAMPLE 8

Figure 19A:
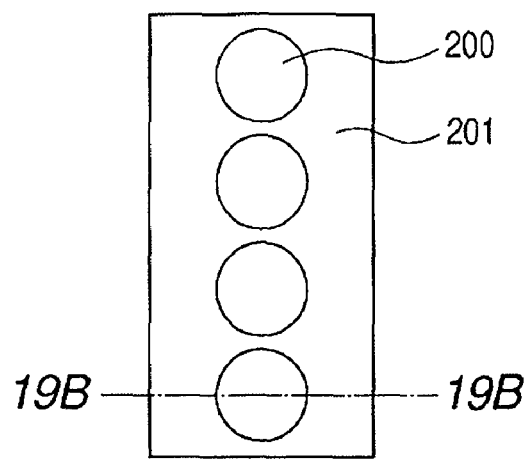
FIGS. 19A, 19B, and 19C are diagram illustrating examples of membrane filters using a total-reflection prism coupler.
Figure 19B:
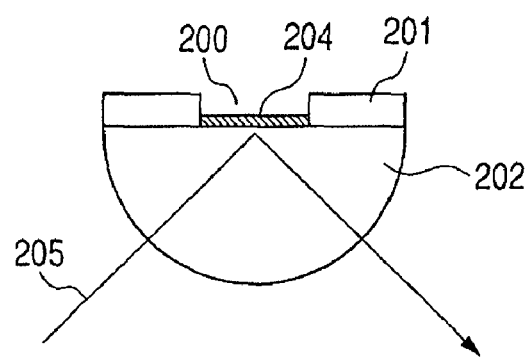
Figure 19C:
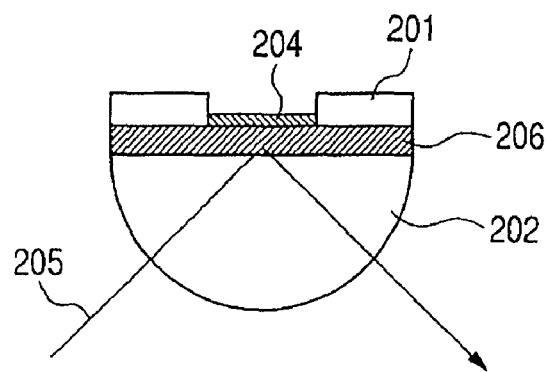

Example 8 of the present invention will be described by referring to FIGS. 19A to 19C. In Example 2, detection was performed by using a terahertz wave reflected by the surface of a membrane filter. In contrast to this, in this Example 8, the sensitivity to a change due to a reflected wave is improved by using an evanescent wave by use of a totally reflecting prism coupler 202. FIG. 19A is a plan view of the prism coupler and FIG. 19B is a sectional view in a portion of FIG. 19A taken along dashed line 19B-19B in FIG. 19A. In FIGS. 19A to 19C, a partition wall member 201 is stuck to a top surface of a semicylindrical prism coupler 202, and a plurality of wells 200 are provided in the partition wall member 201. As the prism coupler 202, a prism made of a high-resistance Si material, which has small losses, dispersion and the like with respect to terahertz waves, is desirably used. However, it is also possible to use dielectric materials, such as magnesium oxide, and resin materials, such as Teflon (registered trademark), as this material. Thus, the configuration of this example is such that the porous materials are disposed in the vicinity of the surface of the prism coupler 202, which is a member that totally reflects an electromagnetic wave, whereby information on the analytes held by the porous materials is obtained.

In the above-described configuration, as shown in FIG. 19B, when a terahertz wave 205 is made incident on the coupler 202, a reflected terahertz wave exits and an evanescent wave is generated in the vicinity of the reflective surface. Therefore, by disposing membrane filters 204 in the wells 200 and supplying analytes thereto, the evanescent wave and the analytes perform interaction, so that high-sensitivity measurement can be made.

The partition wall member 201 as a support member is a member provided to perform high-speed measurement by arranging, as shown in FIG. 19A, the wells 200 to which a plurality of analytes are supplied as described in Example 3. In this example, it is preferred that the membrane filter 204 be about 50 $\mu$m thick in order to ensure that the analytes perform efficient interaction with the evanescent wave. As the total measuring system, it is possible to adopt the same total measuring system as described in Example 2, which is shown in FIG. 6. Although one beam path of the terahertz wave is shown in FIG. 19B, the configuration may be such that multiple reflection is caused in the analyte holding portion.

Also, as a method that has a higher efficiency than an evanescent wave using total reflection, there is used one in which as shown in FIG. 19C, an electrically conductive material 206 is interposed between a membrane filter 204 and the surface of the coupler 202. An electrically conductive material on which an n-type Si thin film (thickness: 2.5 $\mu$m) is deposited is advantageously used as this electrically conductive material 206, and surface plasmon is generated at a frequency near 3 THz. However, those obtained by doping an impurity in other semiconductors, such as InAs and GaAs, and metals, such as Au and Al, may also be used as this electrically conductive material 206.

When membrane filters 204 having a thickness of about 50 $\mu$m are disposed on the surface in the same way as described above, there exists an angle at which a dip having strong absorption of the reflected terahertz wave appears sensitively reflecting the state of the analyte. A change in this angle are detected. By making such measurement, the state of the analyte can be evaluated with good sensitivity. This example is a configuration in which the electrically conductive material 206 is disposed between an analyte and a totally reflecting surface, which is called the Kretschmann configuration. It is also possible to adopt a configuration in which, in contrast, a membrane filter containing an analyte is disposed between a totally reflecting surface and an electrically conductive material, which is called the Otto configuration (not shown). In this case, there is not limit to the thickness of the electrically conductive material. However, when measurement is made at 1 THz, it is preferred that the intervals at which the membrane filters are disposed be not more than about 10 $\mu$m. Also in this case, a multiple reflection structure may be used.

EXAMPLE 9

Example 9 of the present invention will be described. In this example, a membrane filter is used to evaluate a nucleic acid base and a compound containing a nucleic acid base. The term "compound containing a nucleic acid base" herein employed refers to a nucleoside composed of a nucleic acid base bonded to sugar, a nucleotide composed of a nucleic acid base bonded to sugar which is further bonded to phosphoric acid, or the like. The materials used in this example are nucleosides, such as cytosine hydrochloride (C.HCl), deoxycytidine (dC), deoxycytidine hydrochloride (dC.HCl), 5-methyl-deoxycytidine (M-dC), and 5-methyl-cytosine hydrochloride (MC.HCl). Each of these materials is dissolved in pure water and the aqueous solution of an amount containing about 2 $\mu$mol of the material is dropped as a droplet onto the membrane filter and dried.

Figure 20A:
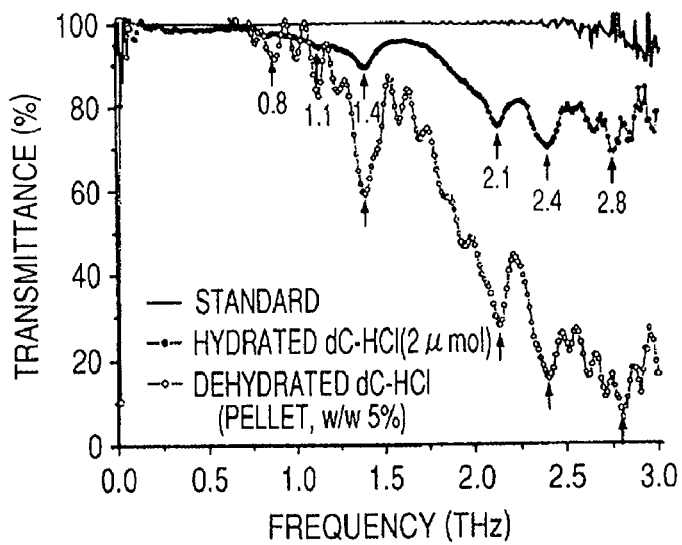
FIGS. 20A, 20B, and 20C are graphical representation showing transmittance spectra of compounds containing a nucleic acid base.
Figure 20B:
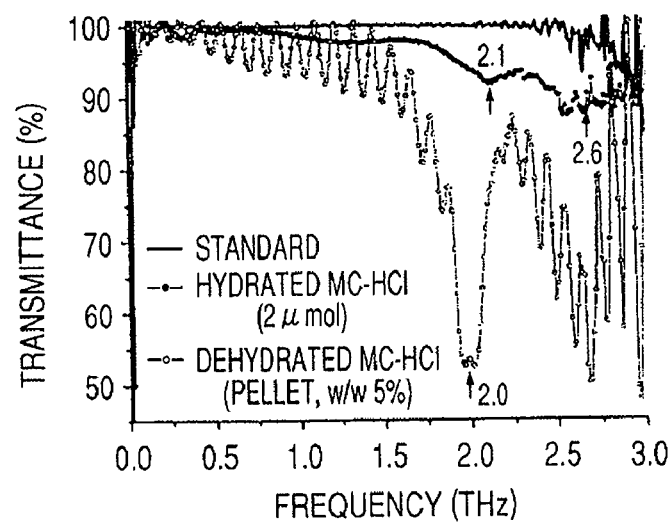
Figure 20C:
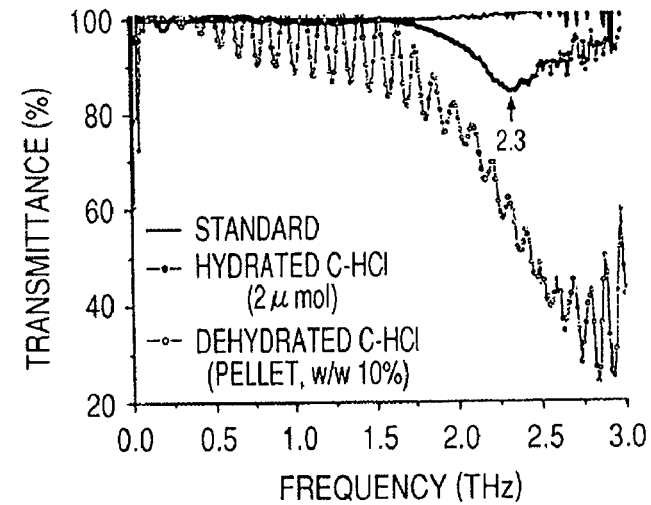

At that time, flat transmission characteristics were observed for dC and M-dC, whereas for the three kinds of samples of hydrochlorides, characteristic absorption spectra, i.e., fingerprint spectra were observed as shown in FIGS. 20A to 20C. In the figures, the data indicated as "Hydrated" were obtained for aqueous solutions and were measured by the method of the present invention, and the data indicated as "Dehydrated" were measured on pellets prepared by mixing solid power of the material with polyethylene powder and compressing the mixed powder. From FIG. 20A, absorption peaks of dC.HCL are observed at frequencies near 0.8 THz, 1.1 THz, 1.4 THz, 2.1 THz, 2.4 THz, and 2.8 THz, from FIG. 20B, absorption peaks of MC.HCl are observed at frequencies near 2.1 THz and 2.6 THz, and from FIG. 20C, an absorption peak of C.HCl is observed at a frequency near 2.3 THz. Thus, fingerprint spectra peculiar to the terahertz wave region were observed. Incidentally, also in this measurement, as described in Example 3, the alternate measurement was made a plurality of times between a reference well (well having only double distilled water (DDW) dropped therein) and other wells having the analyte dropped therein, and the differences between the reference well and other wells were averaged and outputted as a result.

As is seen from FIGS. 20A to 20C, some of the fingerprint spectra of the dissolved materials show the same spectra as in the case where the same material that is not dissolved and in powder form is mixed with polyethylene powder and formed into pellets and then subjected to transmission measurement by a usual method. Therefore, it is considered that in such case, the spectrum may be derived from vibrations within molecules related to the bonding of HCl. In this manner, great changes in spectra are observed only due to the bonding of HCl molecules to nucleosides, so that it is seen that an analysis using a membrane filter by means of a terahertz wave can be made.

Figure 21A:
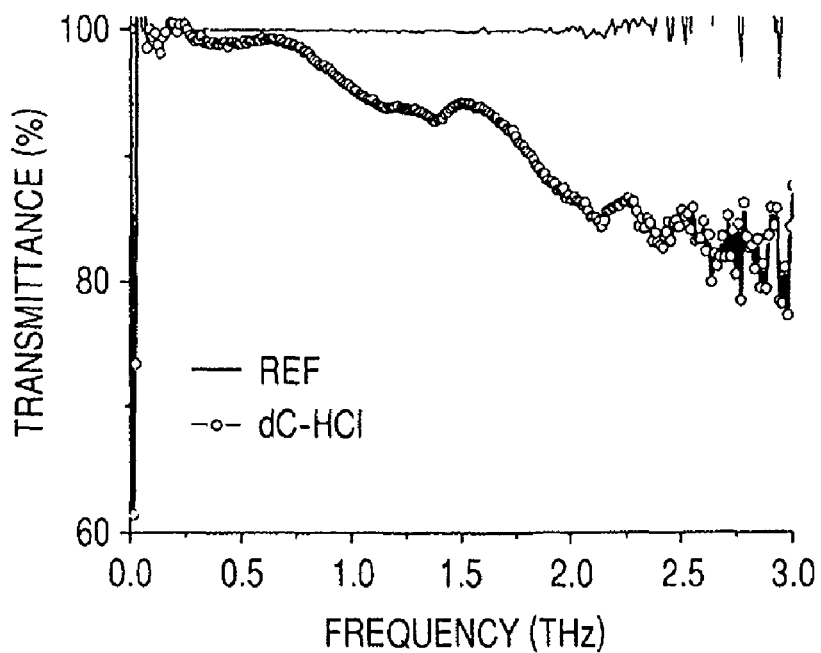
FIGS. 21A and 21B are graphical representation showing comparative examples of transmittance spectra of compounds containing a nucleic acid base, which were measured by using a conventional membrane filter.
Figure 21B:
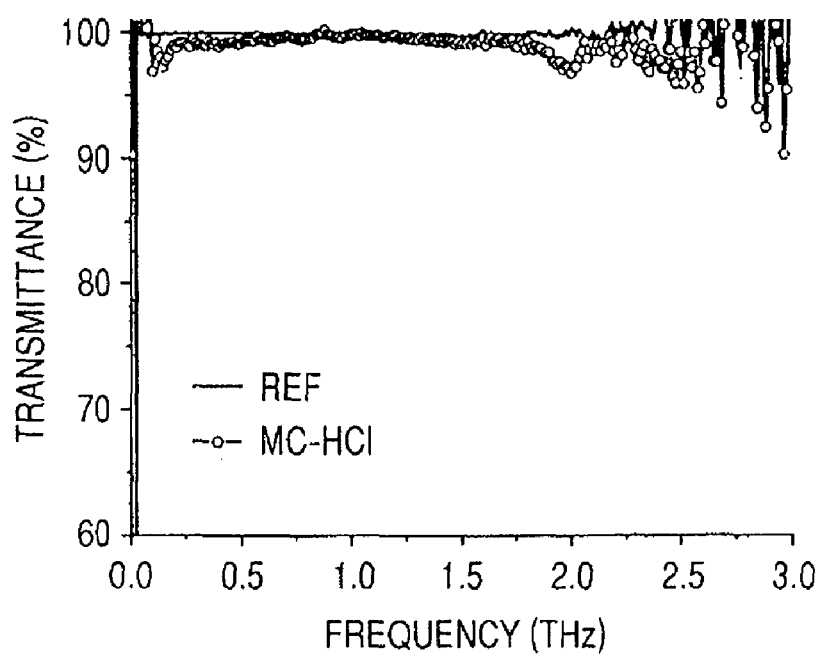

As already described, in the method of the present invention, a membrane filter that enables an analyte to be uniformly distributed was used and, therefore, clear fingerprint spectra were observed as in this example. As comparative examples, measurements were made also for membrane filters formed from nitrocellulose containing a fibrous structure. FIGS. 21A and 21B respectively show results of transmittance obtained in cases where an analyte is prepared for dC.HCl and MC.HCl under completely the same conditions and nitrocellulose is used as the material for the membrane filter. It is seen that compared to the data of FIGS. 20A to 20C, part of the absorption peaks are observable in the form of lowered signal intensity, that is, at frequencies of 1.4 THz, 2.1 THz, and 2.4 THz for dC.HCl and at a frequency of 2.1 THz for MC.HCl, whereas some absorption peaks are not observed at all. Therefore, it is seen that the performance of terahertz spectrometry is improved by the measurement of liquid substances according to the present invention.

Although nucleosides were used in this example, also with nucleotides and molecules in which nucleotides are bonded, it is also possible to perform analysis of slight molecular bonding. Also, DNA and RNA are formed by the bonding thereof. Therefore, when discriminating part of structures of DNA and RNA, it is effective to adopt the method of the present invention that involves dropping a solution onto a membrane filter for measurement.

The materials for analysis are not limited to sugars, proteins, nucleic aid bases, DNA, RNA, and compounds of them which are enumerated in the examples and embodiment above, and for the materials eaten by living things as described below, it is effective to apply the method of the present invention to the lysates and solutions of these materials and to perform analysis of their components. That is, these materials include those related to the human body, such as amino acids, fungal forms, viruses, bloods, and cells, food additives, pigments, and antibiotics. Furthermore, they include drugs and medicines, such as statin drugs (pravastatin, simvastatin, atorvastatin, etc.), angiotensin II receptor antagonists (losartan, candesartan, valsartan, etc.), and proton pump inhibitors (omeprazole, lansoprazole, pantoprazole, etc.). Furthermore, when analysis using a terahertz wave is performed for liquid analytes, such as solutions and lysates in all materials, such as other organic substances and inorganic substances, the method using a membrane filter according to the present invention is effective.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2006-074927, filed Mar. 17, 2006, No. 2006-178886, filed Jun. 29, 2006, No. 2006-231393, filed Aug. 28, 2006, No. 2006-349234, filed Dec. 26, 2006, which are hereby incorporated by reference herein in their entirety.

What is claimed is:

1. An analysis method of obtaining information on an analyte by using an electromagnetic wave of a frequency including a frequency band which is at least a part of a frequency range of 30 GHz or more and 30 THz or less, the method comprising:
    holding a liquid comprising an analyte in a membrane filter;
    irradiating the analyte held in the membrane filter with an electromagnetic wave; and
    detecting a change in propagation state of the electromagnetic wave due to transmission through or reflection by the membrane filter, and obtaining information about the analyte based on a result of the detection,
    wherein the membrane filter comprises a non-fibrous, isotropic porous material,
    wherein an average pore diameter of a plurality of pores of the porous material is 0.1 μm or more, and
    wherein the analyte is held while being entangled with the plurality of pores of the porous material.

2. The analysis method according to claim 1, wherein the porous material comprises at least one selected from the group consisting of polypropylene, polysulfone, nylon, polyethersulfone, Teflon, polyolefin, polyethylene, polystyrene, and ethylene tetrafluoride resins.

3. The analysis method according to claim 1, wherein after a solution or lysate of a biomolecule is held in the membrane filter and then subjected to drying, the information is obtained.

4. The analysis method according to claim 1, wherein after a biomolecule is held in the membrane filter and the information is obtained, the biomolecule is eluted from the membrane filter for reuse.

5. The analysis method according to claim 1, wherein when detecting the change in the propagation state of the electromagnetic wave due to the reflection by the membrane filter, a member that totally reflects the electromagnetic wave is used, the membrane filter is disposed in the vicinity of a reflective surface of the totally reflecting member, and the information on the analyte held in the membrane filter is obtained.

6. The analysis method according to claim 1, wherein a plurality of the membrane filters at least one of which holds the analyte are disposed on a rotary member rotatable about a center in a plane not parallel to the travel direction of the electromagnetic wave, at locations radially apart by the same distance from the center, the membrane filters are sequentially brought into a detection position by rotating the rotary member, and the change in the propagation state of the electromagnetic wave due to transmission through or reflection by the membrane filters brought into the detection position is sequentially detected.

7. The analysis method according to claim 1, wherein the porous material has an electromagnetic wave amplitude transmittance of 90% or more at 2.0 THz.

8. The analysis method according to claim 1, wherein when an index indicating constancy of the amplitude transmittance with respect to frequency in the frequency band of the electromagnetic wave is defined as the absolute value of a value obtained by subtracting 1 from the amplitude transmittance TM of a frequency near the middle of a terahertz wave frequency band used in the measurement and dividing the resulting value by a difference between the amplitude transmittance TH at the upper limit of the frequency band and the amplitude transmittance TL at the lower limit of the frequency band, the porous material has the index of 20 or more.

9. An analysis apparatus for performing the analysis method set forth in claim 1, comprising an electromagnetic wave irradiating unit for irradiating the membrane filter with the electromagnetic wave, and an electromagnetic wave detecting unit for detecting the change in the propagation state of the electromagnetic wave due to the transmission through or the reflection by the membrane filter.

10. The analysis method according to claim 1, wherein the average pore diameter is 2.0 µm or less.

11. The analysis method according to claim 1, wherein the porous material comprises at least one selected from the group consisting of polypropylene, polysulfone, nylon, and polyethersulfone.

* * * * *